US012673063B2

(12) United States Patent
Arboleda-Velasquez et al.

(10) Patent No.: US 12,673,063 B2
(45) Date of Patent: Jul. 7, 2026

(54) METHODS AND MATERIALS FOR TREATMENT OF FIBROSIS

(71) Applicant: Massachusetts Eye and Ear Infirmary, Boston, MA (US)

(72) Inventors: Joseph F. Arboleda-Velasquez, Newton, MA (US); Leo A. Kim, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 504 days.

(21) Appl. No.: 17/920,502

(22) PCT Filed: Apr. 16, 2021

(86) PCT No.: PCT/US2021/027798
§ 371 (c)(1),
(2) Date: Oct. 21, 2022

(87) PCT Pub. No.: WO2021/216378
PCT Pub. Date: Oct. 28, 2021

(65) Prior Publication Data
US 2023/0190764 A1 Jun. 22, 2023

Related U.S. Application Data

(60) Provisional application No. 63/129,418, filed on Dec. 22, 2020, provisional application No. 63/014,194, filed on Apr. 23, 2020.

(51) Int. Cl.
| | |
|---|---|
| *A61K 31/5513* | (2006.01) |
| *A61K 31/4439* | (2006.01) |
| *A61K 31/7088* | (2006.01) |
| *A61P 11/00* | (2006.01) |

(52) U.S. Cl.
CPC ...... *A61K 31/5513* (2013.01); *A61K 31/4439* (2013.01); *A61K 31/7088* (2013.01); *A61P 11/00* (2018.01)

(58) Field of Classification Search
CPC ............ A61K 31/4439; A61K 31/5513; A61K 31/7088; A61P 11/00; A61P 19/04; A61P 31/14; A61P 43/00
See application file for complete search history.

(56) References Cited

U.S. PATENT DOCUMENTS

| | | | |
|---|---|---|---|
| 3,405,122 A | 10/1968 | Berger et al. |
| 4,309,404 A | 1/1982 | Deneale et al. |
| 4,309,406 A | 1/1982 | Guley et al. |
| 4,521,210 A | 6/1985 | Wong |
| 4,556,552 A | 12/1985 | Porter et al. |
| 4,704,295 A | 11/1987 | Porter et al. |
| 4,816,567 A | 3/1989 | Cabilly et al. |
| 4,853,224 A | 8/1989 | Wong |
| 4,997,652 A | 3/1991 | Wong |
| 5,036,101 A | 7/1991 | Hsu et al. |
| 5,041,438 A | 8/1991 | Hsu |
| 5,141,735 A | 8/1992 | Bellemin et al. |
| 5,164,188 A | 11/1992 | Wong |
| 5,164,376 A | 11/1992 | Hsu et al. |
| 5,443,505 A | 8/1995 | Wong et al. |
| 5,501,856 A | 3/1996 | Ohtori et al. |
| 5,545,806 A | 8/1996 | Lonbera et al. |
| 5,545,807 A | 8/1996 | Surani et al. |
| 5,569,825 A | 10/1996 | Lonbera et al. |
| 5,582,981 A | 12/1996 | Toole et al. |
| 5,625,126 A | 4/1997 | Lonberg et al. |
| 5,633,425 A | 5/1997 | Lonbera et al. |
| 5,641,673 A | 6/1997 | Haseloff et al. |
| 5,641,750 A | 6/1997 | Louis |
| 5,641,773 A | 6/1997 | Pardee et al. |
| 5,661,016 A | 8/1997 | Lonbera et al. |
| 5,731,005 A | 3/1998 | Ottoboni et al. |
| 5,766,242 A | 6/1998 | Wong et al. |
| 5,824,072 A | 10/1998 | Wong |
| 5,837,226 A | 11/1998 | Junaherr et al. |
| 5,869,079 A | 2/1999 | Wong et al. |
| 6,074,661 A | 6/2000 | Oleinik et al. |
| 6,331,313 B1 | 12/2001 | Wong et al. |
| 6,369,116 B1 | 4/2002 | Wong et al. |
| 6,699,493 B2 | 3/2004 | Wong |
| 6,719,971 B1 | 4/2004 | Carter et al. |
| 7,354,574 B2 | 4/2008 | Peyman |
| 8,053,454 B2 | 11/2011 | Kearney et al. |
| 8,293,210 B2 | 10/2012 | Huana et al. |
| 8,484,010 B2 | 7/2013 | Tuszynski et al. |

(Continued)

FOREIGN PATENT DOCUMENTS

| | | |
|---|---|---|
| WO | WO 1993011161 | 6/1993 |
| WO | WO 2003078662 | 9/2003 |

(Continued)

OTHER PUBLICATIONS

Cunningham et al. (PNAS, 2012, 109, 36, 14592-14597). (Year: 2012).*
Haubrich et al. (J of Infectious Diseases, 1995, 1246-1252). (Year: 1996).*
Vanderbilt University, https://news.vumc.org/2024/03/25/vumc-team-finds-potential-treatment-for-kidney-fibrosis/, 2024). (Year: 2024).*
Cleveland Clinic, https://my.clevelandclinic.org/health/diseases/10959-pulmonary-fibrosis, 2025 (Year: 2025).*
Huang,Signal Transduction and Targeted Therapy, 2023, p. 1-20 (Year: 2023).*
Zhang, World J Hepatol Jun. 27, 2023; 15(6): 755-774 (Year: 2023).*
MedicalNews (https://www.medicalnewstoday.com/articles/pulmonary-fibrosis#outlook, 2025 ) (Year: 2025).*

(Continued)

*Primary Examiner* — Umamaheswari Ramachandran
(74) *Attorney, Agent, or Firm* — Fish & Richardson P.C.

(57) ABSTRACT

Described herein are methods for treating and reducing risk of fibrosis, e.g., pulmonary fibrosis, in a subject by administering an inhibitor of RUNX family transcription factor 1 (RUNX1) or core-binding factor subunit beta (CBFβ), e.g., in a subject who has a viral infection.

4 Claims, 18 Drawing Sheets

Specification includes a Sequence Listing.

(56)  References Cited

U.S. PATENT DOCUMENTS

| | | | |
|---|---|---|---|
| 8,697,359 | B1 | 4/2014 | Zhang |
| 9,023,649 | B2 | 5/2015 | Mali et al. |
| 9,074,199 | B1 | 7/2015 | Chavez et al. |
| 9,133,269 | B2 | 9/2015 | McConnell et al. |
| 9,446,048 | B2 | 9/2016 | Liu et al. |
| 10,562,890 | B2 * | 2/2020 | Bushweller .......... C07D 401/14 |
| 11,229,662 | B2 | 1/2022 | Arboleda-Velasquez et al. |
| 2004/0229816 | A1 | 11/2004 | Paris et al. |
| 2006/0034834 | A1 | 2/2006 | Marasco et al. |
| 2006/0257452 | A1 | 11/2006 | Hughes et al. |
| 2006/0264380 | A1 | 11/2006 | Hellstrom et al. |
| 2007/0141066 | A1 | 6/2007 | Phillips et al. |
| 2008/0014180 | A1 | 1/2008 | Lanza et al. |
| 2008/0131484 | A1 | 6/2008 | Robinson et al. |
| 2009/0203011 | A1 | 8/2009 | Liebenberg et al. |
| 2009/0220488 | A1 | 9/2009 | Gardner |
| 2009/0285786 | A1 | 11/2009 | Zon et al. |
| 2010/0143380 | A1 | 6/2010 | Crabb et al. |
| 2010/0233194 | A1 | 9/2010 | Combal et al. |
| 2010/0330114 | A1 | 12/2010 | Verdin et al. |
| 2011/0305641 | A1 | 12/2011 | Kazlauskas et al. |
| 2013/0156795 | A1 | 6/2013 | Iavarone et al. |
| 2014/0004082 | A1 | 1/2014 | Liu et al. |
| 2014/0249135 | A1 | 9/2014 | Buraer et al. |
| 2015/0174138 | A1 | 6/2015 | Bernstein et al. |
| 2019/0350961 | A1 | 11/2019 | Arboleda-Velasquez et al. |
| 2020/0102384 | A1 | 4/2020 | Arboleda-Velasquez et al. |
| 2020/0103419 | A1 | 4/2020 | Arboleda-Velasquez et al. |
| 2020/0375899 | A1 | 12/2020 | Kim et al. |
| 2020/0377888 | A1 | 12/2020 | Kim et al. |
| 2022/0341915 | A1 * | 10/2022 | Tata ..................... C12N 5/0688 |
| 2023/0190959 | A1 | 6/2023 | Arboleda-Velasquez |
| 2023/0310446 | A1 | 10/2023 | Kim et al. |

FOREIGN PATENT DOCUMENTS

| | | | | |
|---|---|---|---|---|
| WO | WO 2007017065 | | 2/2007 | |
| WO | WO 2008130315 | | 10/2008 | |
| WO | WO 2009146456 | | 12/2009 | |
| WO | WO 2009152901 | | 12/2009 | |
| WO | WO 2011163669 | | 12/2011 | |
| WO | WO 2012174419 | | 12/2012 | |
| WO | WO 2015049356 | | 4/2015 | |
| WO | WO 2016025744 | | 2/2016 | |
| WO | WO 2016182904 | | 11/2016 | |
| WO | WO 2017112823 | | 6/2017 | |
| WO | WO 2017117538 | A1 | 7/2017 | |
| WO | WO 2018183216 | | 10/2018 | |
| WO | WO-2019040448 | A1 * | 2/2019 | ......... A61K 31/5513 |
| WO | WO 2019099560 | | 5/2019 | |
| WO | WO 2021062412 | | 4/2021 | |

OTHER PUBLICATIONS

Partial European Search Report in European Appln. No. 21791849.9, dated Mar. 7, 2024, 14 pages.

Illendula et al., "A small-molecule inhibitor of the aberrant transcription factor CBFβ-SMMHC delays leukemia in mice," Science, Feb. 2015, 347(6223):779-84.

Office Action in Japanese Appln. No. 2022-564401, mailed on May 20, 2025, 12 pages (with English Translation).

[No Author Listed], "Retinopathy of Prematurity," American Association for Pediatric Ophthalmology and Strabismus, retrieved from URL<https://aapos.org/glossary/retinopathy-of-prematurity>, available on or before Apr. 2020, 4 pages.

Ackermann et al., "Pulmonary Vascular Endothelialitis, Thrombosis, and Angiogenesis in Covid-19," New England Journal of Medicine, Jul. 2020, 383(2):120-8.

Alder et al., "Diagnostic utility of telomere length testing in a hospital-based setting," Proceedings of the National Academy of Sciences of the United States of America, Mar. 2018, 115(10):E2358-E2365.

Antonetti et al., "Vascular Endothelial Growth Factor Induces Rapid Phosphorylation of Tight Junction Proteins Occludin and Zonula Occluden 1," J Biol Chem., Aug. 1999, 274(33):23463-23467.

Arevalo et al., "Tractional Retinal Detachment Following Intravitreal Bevacizumab (Avastin) in Patients With Severe Proliferative Diabetic Retinopathy," Br. J. Ophthalmol., Feb. 2008, 92(2):213-216.

Barberis et al., "Discovery of N-Substituted 7-Azaindoles as Pan-PIM Kinase Inhibitors—Lead Series Identification—Part II," Bioorganic & Medicinal Chemistry Letters, Sep. 2017, 27(20):4735-4740.

Bataille et al., "Thiazolidine Derivatives as Potent and Selective Inhibitors of the PIM Kinase Family," Bioorganic & Medicinal Chemistry, May 2017, 25(9):2657-2665.

Bataller and Brenner, "Liver fibrosis," J Clin Invest., Feb. 2005, 15(2):209-18.

Beigel et al., "Remdesivir for the Treatment of Covid-19—Final Report," New England Journal of Medicine, Nov. 2020, 383(19):1813-26, 14 pages.

Bellissimo et al., "Runx1 negatively regulates inflammatory cytokine production by neutrophils in response to Toll-like receptor signaling," Blood Advances, Mar. 2020, 4(6):1145-58.

Belser et al., "Ocular tropism of respiratory viruses," Microbiol Mol Biol Rev., Mar. 2013, 77(1):144-56.

Berge et al., "Pharmaceutical Salts", Journal of Pharmaceutical Sciences, Jan. 1977, 66(1):1-19.

Bergers et al., "Tumorigenesis and the Angiogenic Switch," Nature Reviews Cancer, Jun. 2003, 3(6):401-410.

Blackwell et al., "Sequence-specific DNA Binding by the c-Myc Protein," Science, Nov. 1990, 250(4984):1149-1151.

Boerner et al., "Production of Antigen-Specific Human Monoclonal Antibodies from in Vitro-Primed Human Splenocytes," J. Immunol., Jul. 1991, 147(1):86-95.

Bonniaud et al., "Smad3 Null Mice Develop Airspace Enlargement and Are Resistant to TGF-β-Mediated Pulmonary Fibrosis," The Journal of Immunology, Aug. 2004, 173(3):2099, 11 pages.

Boyd, "Diabetic Retinopathy Diagnosis," American Academy of Ophthamology, 2013, retrieved on Sep. 8, 2020, retrieved from URL <https://www.aao.org/eye-health/diseases/diabetic-retinopathy-diagnosis>, 6 pages.

Bravo et al., "The leukemia-associated AML1 (Runx1)-CBFbeta complex functions as a DNA-induced molecular clamp," Nature Structural Biology, Apr. 2001, 8(4):371-8.

Burns et al., "Hematopoietic Stem Cell Fate Is Established by the Notch-Runx Pathway," Genes & Development, Oct. 2005, 19(19):2331-2342.

Butko et al., "Complex regulation of HSC emergence by the Notch signaling pathway," Dev. Biol., Jan. 2016, 409(1):129-138.

Castilla et al., "Failure of Embryonic Hematopoiesis and Lethal Hemorrhages in Mouse Embryos Heterozygous for a Knocked-In Leukemia Gene CBFB-MYH11," Cell, Nov. 1996, 87(4):687- 696.

Chang et al., "PIM Kinase Inhibitors Downregulate STAT3Tyr705 Phosphorylation," Mol Cancer Ther., Sep. 2010, 9(9):2478-2487.

Cheema et al., "Keratoconjunctivitis as the initial medical presentation of the novel coronavirus disease 2019 (COVID-19)," Can J Ophthalmol., Aug. 2020, 55(4):e125-e129.

Cheloufi et al., "A Dicer-independent miRNA biogenesis pathway that requires Ago catalysis," Nature, Jun. 2010, 465(7298):584-589.

Chen et al., "Intracellular Antibodies as a New Class of Therapeutic Molecules for Gene Therapy," Human Gene Therapy, 1994, 5(5):595-601.

Chen et al., "Ocular manifestations of a hospitalised patient with confirmed 2019 novel coronavirus disease," Br J Ophthalmol., Jun. 2020, 104(6):748-751.

Chen et al., "Runx1 is required for the endothelial to haematopoietic cell transition but not thereafter," Nature, Feb. 2009, 457(7231):887-891.

Chothia et al., "Canonical Structures for the Hypervariable Regions of Immunoglobulins," J. Mol. Biol., Aug. 1987, 196(4):901-917.

Chothia et al., "Conformations of immunoglobulin hypervariable regions," Nature, Dec. 1989, 342:877-883.

Chung et al., "Developmental and Pathological Angiogenesis," Annu. Rev. Cell Dev. Biol., Nov. 2011, 27:563-584.

Cole, "Monoclonal Antibodies," Can. Fam. Physician, 1987, 33:369-372.

(56)                    References Cited

OTHER PUBLICATIONS

Colyer et al., "Perforating globe injuries during operation Iraqi Freedom," Ophthalmology, 2008, 115:2087-2093.
Connor et al., "Quantification of oxygen-induced retinopathy in the mouse: a model of vessel loss, vessel regrowth and pathological angiogenesis," Nat Protoc., Oct. 2009, 4(11):1565-1573.
Cunningham et al., "Identification of benzodiazepine Ro5-3335 as an inhibitor of CBF leukemia through quantitative high throughput screen against RUNX1-CBFβ interaction," PNAS, Sep. 2012, 109(36):14592-14597.
Daxer, "The Fractal Geometry of Proliferative Diabetic Retinopathy: Implications for the Diagnosis and the Process of Retinal Vasculogenesis," Current Eye Research, Dec. 1993, 12(12):1103-1109.
Delgado-Tirado et al., "Topical delivery of a small molecule RUNX1 transcription factor inhibitor for the treatment of proliferative vitreoretinopathy," Scientific Reports, Nov. 2020, 10(1):20554, 15 pages.
Diabetes Control and Complications Trial Research Group, "The Relationship of Glycemic Exposure (HbA1c) to the Risk of Development and Progression of Retinopathy in the Diabetes Control and Complications Trial," Diabetes, Aug. 1995, 44(8):968-983.
Dua et al., "The ocular surface as part of the mucosal immune system: conjunctival mucosa-specific lymphocytes in ocular surface pathology," Eye (Lond.), 1995, 9(Pt 3):261-7.
Dubois et al., "Evidence that furin is an authentic transforming growth factor-beta1-converting enzyme," Am J Pathol., Jan. 2001, 158(1):305-16.
Eapen et al., "Endothelial to mesenchymal transition: a precursor to post-COVID-19 interstitial pulmonary fibrosis and vascular obliteration?," European Respiratory Journal, Oct. 2020, 56(4):2003167, 3 pages.
Edgar et al., "Gene Expression Omnibus: NCBI gene expression and hybridization array data repository," Nucleic Acids Research, Jan. 2002, 30(1):207-210.
Elbashir et al., "Functional anatomy of siRNAs for mediating efficient RNAi in Drosophila melanogaster embryo lysate," The EMBO Journal, Dec. 2001, 20(23):6877-6888.
Eliott et al., "Smoking is a risk factor for proliferative vitreoretinopathy after traumatic retinal detachment," Retina, 2017, 37(7):1229-1235.
Espinoza et al., "Notch Inhibitors for Cancer Treatment," Pharmacol Ther., Aug. 2013, 139(2):95-110.
Eye.Hms.Harvard.edu [online], "Harvard Medical School Dept. of Ophthalmology Home/News," Apr. 2017, retrieved on Dec. 10, 2021, retrieved from URL<https://eye.hms.harvard.edu/news/researchers-identify-new-target-abnormal-blood-vessel-growth-eyes>, 3 pages.
Fehniger et al., "Single-agent lenalidomide induces complete remission of acute myeloid leukemia in patients with isolated trisomy 13," Blood, 2009, 113(5):1002-1005.
Fire et al., "Potent and Specific Genetic Interference by Double-Stranded RNA in Caenorhabditis Elegans," Nature, 1998, 391:806-810.
Fishwild et al., "High-Avidity Human IgG Kappa Monoclonal Antibodies from a Novel Strain of Minilocus Transgenic Mice," Nature Biotechnology, Aug. 1996, 14(7):845-851.
Frangogiannis, "Fibroblast-Extracellular Matrix Interactions in Tissue Fibrosis," HHS Public Access Author Manuscript, doi:10.1007/s40139-016-0099-1, published online Feb. 5, 2016, 14 pages; Published in final edited form as: Curr Pathobiol Rep., Mar. 2016, 4(1):11-18.
Fräter-Schröder et al., "Tumor necrosis factor type alpha, a potent inhibitor of endothelial cell growth in vitro, is angiogenic in vivo," Proc Natl Acad Sci USA, Aug. 1987, 84(15):5277-81.
Friedlander, "Fibrosis and diseases of the eye," J Clin Invest., 2007, 117(3):576-586.
Geback et al., "TScratch: A novel and simple software tool for automated analysis of monolayer wound healing assays," Biotechniques, Apr. 2009, 46(4):265-274.

GenBank Accession No. AAI41856.1, "Pim-3 oncogene [Homo sapiens]," May 8, 2007, 2 pages.
GenBank Accession No. AB114795.1, "Homo sapiens pim-3 mRNA for serine/threonine kinase Pim-3, Complete cds, " Nov. 9, 2017, 2 pages.
GenBank Accession No. AK292005.1, "Homo sapiens cDNA FLJ75766 complete cds, highly similar to Homo sapiens pim-3 oncogene (PIM3), mRNA," Jan. 9, 2008, 2 pages.
GenBank Accession No. BAD42438.1, "serine/threonine kinase Pim-3 [Homo sapiens]," Nov. 9, 2017, 1 page.
GenBank Accession No. BAF84694.1, "Unnamed protein product [Homo sapiens]," Jan. 9, 2008, 2 pages.
GenBank Accession No. BC141855.1, "Homo sapiens pim-3 oncogene, mRNA (cDNA clone MGC: 167042 IMAGE:8860375), complete cds," May 8, 2007, 2 pages.
GenBank Accession No. NM_000598.4, "Homo sapiens insulin like growth factor binding protein 3 (IGFBP3), transcript variant 2, mRNA," May 28, 2019, 4 pages.
GenBank Accession No. NM_001001852.4, "Homo sapiens Pim-3 proto-oncogene, serine/threonine kinase (PIM3), mRNA," May 8, 2020, 4 pages.
GenBank Accession No. NM_001001890.2, "Homo Sapiens RUNX Family Transcription Factor 1 (RUNX1), Transcript Variant 2, mRNA," May 28, 2019, 8 pages.
GenBank Accession No. NM_001013398.1, "Homo sapiens insulin like growth factor binding protein 3 (IGFBP3), transcript variant 1, mRNA," Oct. 13, 2018, 4 pages.
GenBank Accession No. NM_001122607.2, "Homo Sapiens RUNX Family Transcription Factor 1 (RUNX1), Transcript Variant 3, mRNA", Jun. 7, 2020, 4 pages.
GenBank Accession No. NM_001754.4, "Homo Sapiens RUNX Family Transcription Factor 1 (RUNX1), Transcript Variant 1, mRNA," Feb. 9, 2020, 6 pages.
GenBank Accession No. NP_000589.2, "Insulin-like growth factor-binding protein 3 isoform b precursor [Homo sapiens]," Jun. 14, 2020, 3 pages.
GenBank Accession No. NP_001013416.1, "Insulin-like growth factor-binding protein 3 isoform a precursor [Homo sapiens]," Jun. 14, 2020, 3 pages.
GenBank Accession No. XM_005261068.3, "Predicted: Homo Sapiens RUNX Family Transcription Factor 1 (RUNX1), Transcript Variant X2, mRNA," May 28, 2020, 3 pages.
GenBank Accession No. XM_005261069.4, "Predicted: Homo sapiens RUNX family transcription factor 1 (RUNX1 ), transcript variant X5, mRNA," May 28, 2020, 3 pages.
GenBank Accession No. XM_011529766.2, "Predicted: Homo sapiens RUNX family transcription factor 1 (RUNX1 ), transcript variant X1, mRNA," May 28, 2020, 3 pages.
GenBank Accession No. XM_011529768.2, "Predicted: Homo sapiens RUNX family transcription factor 1 (RUNX1 ), transcript variant X6, mRNA," May 28, 2020, 3 pages.
GenBank Accession No. XM_011529770.2, "Predicted: Homo Sapiens RUNX Family Transcription Factor 1 (RUNX1), Transcript Variant X8, mRNA", May 28, 2020, 2 pages.
GenBank Accession No. XM_017028487.1, "Predicted: Homo sapiens RUNX family transcription factor 1 (RUNX1 ), transcript variant X4, mRNA," May 28, 2020, 3 pages.
GenBank Accession No. XR_937576.2, "PREDICTED: Homo sapiens RUNX family transcription factor 1 (RUNX1), transcript variant X7, misc_RNA", May 28, 2020, 3 pages.
George et al., "Pulmonary fibrosis and COVID-19: the potential role for antifibrotic therapy," The Lancet Respiratory Medicine, Aug. 2020, 8(8):807-15.
ghr.nlm.nih.gov [online], "Age-related macular degeneration," Aug. 2016, retrieved from URL <https://ghr.nlm.nih.gov/condition/age-related-macular-degeneration>, 8 pages.
Giani et al., "In Vivo Evaluation of Laser-Induced Choroidal Neovascularization Using Spectral- Domain Optical Coherence Tomography," Investigative Ophthalmology & Visual Science, 2011, 52(6):3880-3887.
Glinsky, "Tripartite Combination of Candidate Pandemic Mitigation Agents: Vitamin D, Quercetin, and Estradiol Manifest Properties of Medicinal Agents for Targeted Mitigation of the COVID-19

(56) References Cited

OTHER PUBLICATIONS

Pandemic Defined by Genomics-Guided Tracing of SARS-CoV-2 Targets in Human Cells," Biomedicines, May 2020, 8(5):129, 26 pages.

Graney and Lee, "Impact of novel antifibrotic therapy on patient outcomes in idiopathic pulmonary fibrosis: patient selection and perspectives," Patient Relat Outcome Meas., 2018, 9:321-8.

Hakeem et al., "Retinopathy of Prematurity: A Study of Prevalence and Risk Factors," Middle East African Journal of Ophthalmology, 2012, 19(3):289-294.

Harris et al., "Glucose Metabolism Impacts the Spatiotemporal Onset and Magnitude of HSC Induction in Vivo," Blood, Mar. 2013, 121(13):2483-2493.

Haubrich et al., "A Randomized Trial of the Activity and Safety of Ro 24-7429 (Tat Antagonist) Versus Nucleoside for Human Immunodeficiency Virus Infection," The Journal of Infectious Diseases, Nov. 1995, 172(5): 1246-1252.

Heckl et al., "Generation of mouse models of myeloid malignancy with combinatorial genetic lesions using CRISPR-Cas9 genome editing," Nat. Biotechnol., 2014, 32(9):941-946, 14 pages.

Hendren et al., "Description and Proposed Management of the Acute COVID-19 Cardiovascular Syndrome," Circulation, Apr. 2020, 141(23):1903-1914, 19 pages.

Holliger et al., "'Diabodies': Small Bivalent and Bispecific Antibody Fragments," Proceedings of the National Academy of Sciences of the United States of America, Jul. 1993, 90(14):6444-6448.

Hong et al., "Runx1 stabilizes the mammary epithelial cell phenotype and prevents epithelial to mesenchymal transition," Oncotarget, Mar. 2017, 8(11):17610-17627.

Hoogenboom et al., "By-Passing immunisation: Human Antibodies from Synthetic Repertoires of Germline VH Gene Segments Rearranged in Vitro," Journal of Molecular Biology, Sep. 1992, 227(2):381-388.

Hoyt et al., "Alterations in pulmonary mRNA encoding procollagens, fibronectin and transforming growth factor-beta precede bleomycin-induced pulmonary fibrosis in mice," J Pharmacol Exp Ther., Aug. 1988, 246(2):765-71.

Hsu et al., "Combined Tractional and Rhegmatogenous Retinal Detachment in Proliferative Diabetic Retinopathy in the Anti-VEGF Era", Journal of Ophthalmology, Jun. 2014, Article ID 917375, 2014(7):11 pages.

Hsu et al., "Inhibition of type 1 human immunodeficiency virus replication by a tat antagonist to which the virus remains sensitive after prolonged exposure in vitro," Proc Natl Acad Sci USA, Jun. 1993, 90(14):6395-9.

Huang et al., "Bioinformatics Enrichment Tools: Paths Toward the Comprehensive Functional Analysis of Large Gene Lists," Nucleic Acids Research, Jan. 2009, 37(1):1-13.

Huertas et al., "Endothelial cell dysfunction: a major player in SARS-CoV-2 infection (COVID-19)?," European Respiratory Journal, Jul. 2020, 56(1):2001634, 5 pages.

Hutchinson et al., "Global incidence and mortality of idiopathic pulmonary fibrosis: a systematic review," European Respiratory Journal, Sep. 2015, 46(3):795-806.

Illendula et al., "Small Molecule Inhibitor of CBF~-RUNX Binding for RUNX Transcription Factor Driven Cancers," EBioMedicine, Nov. 2017, 8:117-131.

Imanirad et al., "HIF1α is a Regulator of Hematopoietic Progenitor and Stem Cell Development in Hypoxic Sites of the Mouse Embryo," Stem Cell Res., Jan. 2014, 12(1):24-35.

International Preliminary Report on Patentability in International Appln. No. PCT/US2017/061620, dated May 21, 2019, 17 pages.

International Preliminary Report on Patentability in International Appln. No. PCT/US2018/061110, dated May 28, 2020, 12 pages.

International Preliminary Report on Patentability in International Appln. No. PCT/US2021/027798, mailed on Nov. 3, 2022, 9 pages.

International Search Report and the Written Opinion in International Appln. No. PCT/US2018/061110, dated Mar. 25, 2019, 17 pages.

International Search Report and Written Opinion in International Appln. No. PCT/US2021/027798, dated Sep. 28, 2021, 13 pages.

International Search Report in International Appln. No. PCT/US2017/061620, dated Mar. 19, 2018, 24 pages.

Ishikawa et al., "Microarray Analysis of Gene Expression in Fibrovascular Membranes Excised From Patients With Proliferative Diabetic Retinopathy," Investigative Ophthalmology & Visual Science, Feb. 2015, 56(2):932-946.

Ito et al., "RUNX Transcription Factors as Key Targets of TGF-beta Superfamily Signaling," Current Opinion in Genetics and Development, Feb. 2003, 13(1):43-47.

Iwatsuki et al., "Runx1 Promotes Angiogenesis by Downregulation of Insulin-Like Growth Factor-Binding Protein-3", Oncogene, Feb. 2005, 24(7):1129-1137.

Ji et al., "Inflammatory regulatory network mediated by the joint action of NF-kB, STAT3, and AP-1 factors is involved in many human cancers," Proceedings of the National Academy of Sciences, May 2019, 116(19):9453-9462.

Jo et al., "Animal Models of Diabetic Retinopathy: Doors to Investigate Pathogenesis and Potential Therapeutics," Journal of Biomedical Science, 2013, 20:38, 13 pages.

Jones et al., "Replacing the Complementarity-Determining Regions in a Human Antibody with those from a Mouse," Nature, May 1986, 321(6069):522-525.

Joyce, "Amplification, Mutation and Selection of Catalytic RNA," Gene, Oct. 1989, 82(1):83-87.

Kalev-Zylinska et al., "Runx1 is Required for Zebrafish Blood and Vessel Development and Expression of a Human RUNX1-CBF2T1 Transgene Advances a Model for Studies of Leukemogenesis," Development, 2002, 129(8):2015-2030.

Kategaya et al., "USP7 Small-Molecule Inhibitors Interfere With Ubiquitin Binding," Nature, Oct. 2017, 550(7677):534-538, 33 pages.

Kim et al., "A Brief History of Anti-VEGF for the Treatment of Ocular Angiogenesis," The American Journal of Pathology, 2012, 181(2):376-379.

Kim et al., "Characterization of Cells from Patient-Derived Fibrovascular Membranes in Proliferative Diabetic Retinopathy," Molecular Vision, Jun. 2015, 21:673-687.

Kim et al., "Inhibition of Runx1 by the Ro5-3335 benzodiazepine derivative reduces aberrant retinal angiogenesis," Abstract, Presented at Annual Meeting of the Association for Research in Vision and Ophthalmology (ARVO), Baltimore, MD, USA; May 7-11, 2017; IOVS, Jun. 2017, 58(8):4029, 3 pages.

Kim et al., "Pim-1 Kinase Phosphorylates and Stabilizes RUNX3 and Alters Its Subcellular Localization," Journal of Cellular Biochemistry, Nov. 2008, 105(4):1048-1055.

Kim et al., "RUNX1 is essential for mesenchymal stem cell proliferation and myofibroblast differentiation," Proc Natl Acad Sci USA, Nov. 2014, 111(46):16389-94.

Köhler et al., "Continuous Cultures of Fused Cells Secreting Antibody of Predefined Specificity," Nature, Aug. 1975, 256(5517):495-497.

Kozlowski et al., "A Human Melanoma Line Heterogeneous With Respect to Metastatic Capacity in Athymic Nude Mice," Journal of the National Cancer Institute, Apr. 1984, 72(4):913-917.

Kuiper et al., "The Angio-Fibrotic Switch of VEGF and CTGF in Proliferative Diabetic Retinopathy," PLoS ONE, Jul. 2008, 3(7):e2675, 7 pages.

Lam et al., "Identification of RUNX1 as a Mediator of Aberrant Retinal Angiogenesis," Diabetes, 2017, 66:1950-1956.

Lederer et al., "Idiopathic Pulmonary Fibrosis," New England Journal of Medicine, May 2018, 378(19):1811-23.

Lee et al., "TGF-β regulates cell fate during epithelial-mesenchymal transition by upregulating survivin," Cell Death & Disease, Jul. 2013, 4(7):e714, 10 pages.

Li et al., "RUNX1 promotes tumour metastasis by activating the WNT/beta-catenin signalling pathway and EMT in colorectal cancer," J Exp Clin Cancer Res, Aug. 2019, 38(1):334, 13 pages.

Liang et al., "In Vitro Scratch Assay: A Convenient and Inexpensive Method for Analysis of Cell Migration in Vitro," Nature Protocols, Mar. 2007, 2(2):329-333.

Liberati et al., "Smads bind directly to the Jun family of AP-1 transcription factors," Proc Natl Acad Sci USA, Apr. 1999, 96(9):4844-9.

(56)          References Cited

OTHER PUBLICATIONS

Lichtinger et al., "Chromatin Regulation by RUNX1," Blood Cells, Molecules and Diseases, Apr. 2010, 44(4):287-290.

Lie-A-Ling et al., "RUNX1 Positively Regulates a Cell Adhesion and Migration Program in Murine Hemogenic Endothelium Prior to Blood Emergence," Blood, Sep. 2014, 124(11):e11-e20.

Lin et al., "LncRNA Hoxaas3 promotes lung fibroblast activation and fibrosis by targeting miR-450b-5p to regulate Runx1," Cell Death & Disease, Aug. 2020, 11(8):706, 14 pages.

Liu et al., "Conjunctiva is not a preferred gateway of entry for SARS-CoV-2 to infect respiratory tract," Med Virol., Sep. 2020, 92(9):1410-1412.

Lofqvist et al., "IGFBP3 suppresses retinopathy through suppression of oxygen-induced vessel loss and promotion of vascular regrowth," PNAS, 2007, 104(25):10589-10594.

Lonberg et al., "Antigen-Specific Human Antibodies from Mice Comprising Four Distinct Genetic Modifications," Nature, Apr. 1994, 368:856-859.

Lonberg et al., "Human Antibodies from Transgenic Mice," Intern. Rev. Immunol., 1995, 13(1):65-93.

Lucas et al., "Abstract: Formation of abdominal adhesions is inhibited by antibodies to transforming growth factor-beta 1," J Surg Res., Oct. 1996, 65(2):135-8, 4 pages.

Ludwig, "The Use of Mucoadhesive Polymers in Ocular Drug Delivery," Advanced Drug Delivery Reviews, 2005, 57(11):1595-1639.

Maher, "PROFILEing idiopathic pulmonary fibrosis: rethinking biomarker discovery," European Respiratory Review, Jun. 2013, 22(128):148-52.

Malaviya et al., "Anti-TNFα therapy in inflammatory lung diseases," HHS Public Access Author Manuscript, doi:10.1016/j.pharmthera.2017.06.008, published online Nov. 4, 2017, 23 pages; Published in final edited form as: Pharmacol Ther., Dec. 2017, 180:90-8.

Malaviya et al., "Attenuation of Nitrogen Mustard-Induced Pulmonary Injury and Fibrosis by Anti-Tumor Necrosis Factor-a Antibody," Toxicological Sciences, Nov. 2015, 148(1):71-88.

Marks et al., "By-Passing Immunization: Human Antibodies from V-Gene Libraries Displayed on Phage," J. Mol. Biol., Dec. 1991, 222(3):581-597.

Martin et al., "TGF-β1 and radiation fibrosis: a master switch and a specific therapeutic target?," Int J Radiat Oncol Biol Phys., May 2000, 47(2):277-90.

Martines et al., "Pathology and Pathogenesis of SARS-CoV-2 Associated with Fatal Corona virus Disease, United States," Emerg Infect Dis., Sep. 2020, 26(9):2005-15.

Martinez-Hoyer et al., "RUNX1 Loss of Function Drives Resistance to Lenalidomide in Del(5Q) Myelodysplastic Syndrome Patients," Leukemia Research, 2017, 1(55):S43-S44.

Masoumpour et al., "Current and Future Techniques in Wound Healing Modulation after Glaucoma Filtering Surgeries," Open Ophthalmol J., 2016, 10:68-85.

mayoclinic.org [online], "Diabetic Retinopathy," Mar. 2015, via Internet archive: Wayback Machine URL <http://web.archive.org/web/20180308085607/https://www.mayoclinic.org/diseases-conditions/diabetic-retinopathy/diagnosis-treatment/drc-20371617>, retrieved on Sep. 30, 2021, URL <https://www.mayoclinic.org/diseases-conditions/diabetic-retinopathy/diagnosis-treatment/drc-20371617>, 7 pages.

mayoclinic.org [online], "Dry Macular Degeneration," 2015, retrieved from URL <https://www.mayoclinic.org/diseasesconditions/drymaculardegeneration/diagnosis-treatment/drc-20350381>, 5 pages.

mayoclinic.org [online], "Wet Macular Degeneration," 2015, retrieved from URL <https://www.mayoclinic.org/diseasesconditions/wet-macular-degeneration/diagnosis-treatment/drc-20351113>, 6 pages.

McAuley et al., "Vitreous Biomarkers in Diabetic Retinopathy: A Systematic Review and Meta-Analysis," Journal of Diabetic Complications, 2014, 28(3):419-425.

McLeod et al., "From Blood Islands to Blood Vessels: Morphologic Observations and Expression of Key Molecules during Hyaloid Vascular System Development," Investigative Ophthalmology & Visual Science, Dec. 2012, 53(13):7912-7927.

Medlineplus.gov [online], "Retinal vein occlusion," Available on or before Mar. 6, 2018, retrieved Feb. 22, 2019, retrieved from URL <https://medlineplus.gov/ency/article/007330.htm>, 4 pages.

Michaud et al., "Integrative Analysis of RUNX1 Downstream Pathways and Target Genes," BMC Genomics, Jul. 2008, 9:363, 17 pages.

Morrison, "Success in Specification," Nature, Apr. 1994, 368:812-813.

Moshfeghi et al., "Retinal Capillary Angioma," American Academy of Ophthalmology, Oct. 2013, 7 pages.

Mukhopadhyay et al., "Role of TNFα in pulmonary pathophysiology," Respiratory Research, 2006, 7(1):125, 9 pages.

my.clevelandclinic.org [online], "Retinal Vein Occlusion (RVO)," 2015, retrieved from URL <https://my.clevelandclinic.org/health/diseases/14206-retinal-vein-occlusion-rvo>, 4 pages.

Nakano et al., "Design and Synthesis of an in Vivo-Efficacious PIM3 Kinase Inhibitor as a Candidate Anti-Pancreatic Cancer Agent," Bioorganic & Medicinal Chemistry Letters, Dec. 2015, 25(24):5687-5693.

Namba et al., "Indispensable Role of the Transcription Factor PEBP2/CBF in Angiogenic Activity of a Murine Endothelial Cell MSS31," Oncogene, Jan. 2000, 19(1):106-114.

nei.nih.gov [online], "Facts About Retinopathy of Prematurity (ROP)," National Eye Institute, available on or before Jun. 2014, retrieved on Feb. 22, 2019, retrieved from URL <https://nei.nih.gov/health/rop/rop>, 3 pages.

Neuberger, "Generating High-Avidity Human Mabs in Mice," Nature Biotechnology, Jul. 1996, 14(7):826, 1 page.

Nicholls et al., "An Improved Method for Generating Single-Chain Antibodies From Hybridomas," Journal of Immunological Methods, Sep. 1993, 165(1):81-91.

O'Hare et al., "Targeting Runt-Related Transcription Factor 1 Prevents Pulmonary Fibrosis and Reduces Expression of Severe Acute Respiratory Syndrome Coronavirus 2 Host Mediators," The American Journal of Pathology, Jul. 2021, 191(7):1193-1208.

Ojo et al., "Pulmonary Fibrosis in COVID-19 Survivors: Predictive Factors and Risk Reduction Strategies," Pulmonary Medicine, Aug. 2020, 2020:6175964, 10 pages.

Pandya et al., "Neovascular Glaucoma," Medscape, available on or before Oct. 2016, retrieved from URL <https://emedicine.medscape.com/article/1205736-overview#a6>, 15 pages.

Pashaei et al., "Immunotherapy for SARS-CoV-2: potential opportunities," Expert Opin Biol Ther., Oct. 2020, 20(10):1111-5.

Pettus et al., "Discovery and Optimization of Quinazolinone-pyrrolopyrrolones as Potent and Orally Bioavailable Pan-Pim Kinase Inhibitors," J. Med. Chem., Jun. 2016, 59(13):6407-6430.

Pluckthun, "Antibodies from *Escherichia coli*," The Pharmacology of Monoclonal Antibodies, 1994, 113:269-315.

Polak et al., "A systematic review of pathological findings in COVID-19: a pathophysiological timeline and possible mechanisms of disease progression," Mod Pathol., Nov. 2020, 33(11):2128-38.

Pratt et al., "Abstract 1010: Identification of evolutionarily conserved transcription response elements associated with regulation of cadherin expression in retinal pigment epithelial cells," Molecular Biology of the Cell, 2004, 15(Suppl. S):182A, 1 page.

Presta, "Antibody Engineering," Current Opinion in Structural Biology, 1992, 2(4):593-596.

Rakoczy et al., "Characterization of a Mouse Model of Hyperglycemia and Retinal Neovascularization," The American Journal of Pathology, Nov. 2010, 177(5):2659-2670.

Ran et al., "γ-Secretase Inhibitors in Cancer Clinical Trials are Pharmacologically and Functionally Distinct," EMBO Molecular Medicine, Jul. 2017, 9(7):950-966.

Riddell et al., "RUNX1: an emerging therapeutic target for cardiovascular disease," Cardiovasc Res., Mar. 2020, 116(8):1410-1423.

Riechmann et al., "Reshaping Human Antibodies for Therapy," Nature, Mar. 1988, 332:323-327.

Sainson et al., "TNF primes endothelial cells for angiogenic sprouting by inducing a tip cell phenotype," Blood, May 2008, 111(10):4997-5007.

(56)          References Cited

OTHER PUBLICATIONS

Saint-Geniez et al., "Endogenous VEGF Is Required for Visual Function: Evidence for a Survival Role on Muller Cells and Photoreceptors," PLoS ONE, Nov. 2008, 3(11):e3554, 13 pages.

Sang et al., "Is Blockade of Vascular Endothelial Growth Factor Beneficial for all Types of Diabetic Retinopathy?" Diabetologia, Jul. 2008, 51(9): 1570-1573.

Schaefer et al., "In situ detection of SARS-CoV-2 in lungs and airways of patients with COVID-19," Modern Pathology, Jun. 2020, 33(11):2104-14.

Scholle, "Ocular Ischemic Syndrome," Medscape, 2019, retrieved Sep. 8, 2020, retrieved from URL <https://emedicine.medscape.com/article/1201678-overview>, 3 pages.

Selman et al., "Idiopathic pulmonary fibrosis: an epithelial fibroblastic cross-talk disorder," Respir Res., 2002, 3(1):3, 8 pages.

Shah et al., "Alk5/Runx1 signaling mediated by extracellular vesicles promotes vascular repair in acute respiratory distress syndrome," Clin Transl Med, Jun. 2018, 7(1):19, 18 pages.

Shaki-Loewenstein et al., "A universal strategy for stable intracellular antibodies", Journal of Immunological Methods, Aug. 2005, 303(1-2):19-39.

Shao et al., "Choroid Sprouting Assay: An Ex Vivo Model of Microvascular Angiogenesis, " PLoS ONE, Jul. 2013, 8(7):e69552, 11 pages.

Shazly et al., "Neovascular Glaucoma: Etiology, Diagnosis and Prognosis," Seminars in Ophthalmology, Mar. 2009, 24(2):113-121.

Sinha and Ware, "Selective tumour necrosis factor receptor-1 inhibition in acute lung injury: a new hope or a false dawn?," Thorax, Aug. 2018, 73(8):699-701.

Smith et al., "Oxygen-Induced Retinopathy in the Mouse," Invest Ophthalmol Vis Sci, Jan. 1994, 35(1):101-111.

Sohn et al., "Angiofibrotic Response to Vascular Endothelial Growth Factor Inhibition in Diabetic Retinal Detachment," Arch Ophthalmol, Sep. 2012, 130(9):1127-1134.

Strongman et al., "Incidence, Prevalence, and Survival of Patients with Idiopathic Pulmonary Fibrosis in the UK," Adv Ther., May 2018, 35(5):724-36.

Sui et al., "oPOSSUM: Identification of Over-represented Transcription Factor Binding Sites in Co-Expressed Genes," Nucleic Acids Research, 2005, 33(10):3154-3164.

Tang et al., "Runt-Related Transcription Factor 1 Regulates LPS-Induced Acute Lung Injury via NF-κB Signaling," Am J Respir Cell Mol Biol., 2017, 57(2):174-83.

Tashiro et al., "Exploring Animal Models That Resemble Idiopathic Pulmonary Fibrosis," Frontiers in Medicine, Jul. 2017, 4:118, 11 pages.

Terelak-Borys et al., "Ocular Ischemic Syndrome—A Systematic Review," Med Sci Monit, Aug. 2012, 18(8):RA138-RA144.

The RECOVERY Collaborative Group, "Dexamethasone in Hospitalized Patients with Covid-19—Preliminary Report," New England Journal of Medicine, Feb. 2021, 384(8):693-704, 11 pages.

Thomas, "Furin at the cutting edge: from protein traffic to embryogenesis and disease," HHS Public Access Author Manuscript, doi: 10.1038/nrm934, published online 2002, 32 pages; Published in final edited form as Nat Rev Mol Cell Biol., Oct. 2002, 3(10):753-66.

Tober et al., "Taking the leap: Runx1 in the formation of blood from endothelium," Current Topics in Developmental Biology, Feb. 2016, 118:113-162.

Trapnell et al., "TopHat: Discovering Splice Junctions with RNA-Seq," Bioinformatics, Apr. 2009, 25(9):1105-1111.

Tuerk et al., "Systematic Evolution of Ligands by Exponential Enrichment: RNA Ligands to Bacteriophage T4 DNA Polymerase," Science, Aug. 1990, 249(4968):505-510.

Turell et al., "Vascular Tumors of the Retina and Choroid: Diagnosis and Treatment," Middle East Afr J Ophthalmol., 2010, 17(3):191-200.

Ulrich et al. "CD147 as a Target for COVID-19 Treatment: Suggested Effects 2, 4-6, 19, 21-23 of Azithromycin and Stem Cell Engagement," Stem Cell Reviews and Reports, Apr. 2020, 16:434-440, 7 pages.

UniProt Accession No. P17936, "Insulin-like growth factor-binding protein 3," Nov. 1, 1990, 8 pages.

UniProt Accession No. Q01196-10, "Runt-related transcription factor 1," Apr. 1, 1993, 1 page.

UniProt Accession No. Q01196-11, "RUNX1_Human Isoform AML-1L of Runt-related transcription factor 1," Apr. 1, 1993, 1 page.

UniProt Accession No. Q01196-2, "RUNX1_Human Isoform AML-1A of Runt-related transcription factor 1," Apr. 1, 1993, 1 page.

UniProt Accession No. Q01196-3, "RUNX1_Human Isoform AML-1C of Runt-related transcription factor 1," Apr. 1, 1993, 1 page.

UniProt Accession No. Q01196-4, "RUNX1_Human Isoform AML-1E of Runt-related transcription factor 1," Apr. 1, 1993, 1 page.

UniProt Accession No. Q01196-5, "RUNX1_Human Isoform AML-1FA of Runt-related transcription factor 1," Apr. 1, 1993, 1 page.

UniProt Accession No. Q01196-6, "RUNX1_Human Isoform AML-1FB of Runt-related transcription factor 1," Apr. 1, 1993, 1 page.

UniProt Accession No. Q01196-7, "RUNX1_Human Isoform AML-1FC of Runt-related transcription factor 1," Apr. 1, 1993, 1 page.

UniProt Accession No. Q01196-8, "RUNX1_Human Isoform AML-1G of Runt-related transcription factor 1," Apr. 1, 1993, 1 page.

UniProt Accession No. Q01196-9, "RUNX1_Human Isoform AML-1H of Runt-related transcription factor 1," Apr. 1, 1993, 1 page.

UniProt Accession No. Q86V86, "Serine/threonine-protein kinase pim-3," Nov. 21, 2003, 6 pages.

Van Geest et al., "A Shift in the Balance of Vascular Endothelial Growth Factor and Connective Tissue Growth Factor by Bevacizumab Causes the Angiofibrotic Switch in Proliferative Diabetic Retinopathy," Br J Ophthalmol, Jan. 2012, 96(4):587-590.

Vancheri et al., "Nintedanib with Add-on Pirfenidone in Idiopathic Pulmonary Fibrosis. Results of the INJOURNEY Trial," Am J Respir Crit Care Med., Feb. 2018, 197(3):356-63.

Verhoeyen et al., "Reshaping Human Antibodies: Grafting an Antilysozyme Activity," Science, Mar. 1988, 239(4847):1534-1536.

Wang et al. "Discovery of 5-Azaindole (GNE-955) as a Potent Pan-Pim Inhibitor With Optimized Bioavailability," J. Med. Chem., Apr. 2017, 60(10):4458-4473.

Whitmore et al., "TNF-α signaling regulates RUNX1 function in endothelial cells," The FASEB Journal, Feb. 2021, 35(2):e21155, 17 pages.

Wu et al., "Characteristics of Ocular Findings of Patients With Coronavirus Disease 2019 (COVID-19) in Hubei Province, China," JAMA Ophthalmol., May 2020, 138(5):575-578.

Xie et al., "Single-Cell Deconvolution of Fibroblast Heterogeneity in Mouse Pulmonary Fibrosis," Cell Rep., Mar. 2018, 22(13):3625-40.

Yadav et al., "Tumour Angiogenesis and Angiogenic Inhibitors: A Review," J Clin Diagn Res., Jun. 2015, 9(6):XE01-XE05.

Yan et al., "Feedback regulation of TGF-β signaling," Acta Biochimica et Biophysica Sinica, Jan. 2018, 50(1):37-50.

Yang et al., "Mechanisms of epithelial-mesenchymal transition in proliferative vitreoretinopathy," Discov Med., Oct. 2015, 20(110):207-217, 21 pages.

Yoshida et al., "Gene expression profile of fibrovascular membranes from patients with proliferative diabetic retinopathy," Br J Ophthalmol., 2010, 94(6):795-801.

Yuan et al., "Notch Signaling: An Emerging Therapeutic Target for Cancer Treatment," Cancer Letters, Dec. 2015, 369(1):20-27.

Yue et al., "TGF-β: Titan of Lung Fibrogenesis," HHS Public Access Author Manuscript, doi: 10.2174/10067, Oct. 2013, 20 pages; Published in final edited form as: Curr Enzym Inhib., Jul. 2010, 6(2):10.2174/10067.

Yzaguirre et al., "The Role of Runx1 in Embryonic Blood Cell Formation," RUNX Proteins in Development and Cancer, Singapore: Springer Singapore, Groner et al. (eds.), 2017, pp. 47-64.

Zapata et al., "Engineering Linear F(ab')2 Fragments for Efficient Production in Escherichia coli and Enhanced Anti-Proliferative Activity," Protein Engineering, Oct. 1995, 8(10): 1057-1062.

Zhou et al., "Runt-Related Transcription Factor 1 (RUNX1) Promotes TGF-f3-Induced Renal Tubular Epithelial-to-Mesenchymal Transition (EMT) and Renal Fibrosis through the PI3K Subunit p110δ," EBioMedicine, May 2018, 31:217-25.

(56) References Cited

OTHER PUBLICATIONS

Zhou et al., "RUNX proteins desensitize multiple myeloma to lenalidomide via protecting IKZFs from degradation," Leukemia, 2019, 33:2006-2021.

Extended European Search Report in European Appln. No. 21791849.9, dated May 28, 2024, 12 pages.

Office Action in European Appln. No. 21791849.9, mailed on Jun. 13, 2025, 6 pages.

U.S. Appl. No. 62/906,241, filed Sep. 26, 2019, Tata et al.

U.S. Appl. No. 62/975,294, filed Feb. 12, 2020, Tata et al.

Trujillo et al., "Angiogenesis in acute myeloid leukemia and opportunities for novel therapies," Journal of Oncology, 2012; 2012(1):128608, 9 pages.

Kaelin "Use and abuse of RNAi to study mammalian gene function," Science, Jul. 2012, 337(6093):421-422, 4 pages (Author Manuscript).

Office Action in Chinese Appln. No. 202180044451.3, mailed on Jan. 4, 2026, 16 pages (with English translation).

Third Party Opposition in European Appln. No. 21791849.9, mailed on Dec. 15, 2025, 10 pages.

Office Action in Japanese Appln. No. 2022-564401, mailed on Jan. 6, 2026, 6 pages (with English Translation).

Weiss et al., "Recognizing and exploiting differences between RNAi and small-molecule inhibitors," Nature Chemical Biology, Dec. 2007, 3(12):739-744, 12 pages (Author Manuscript).

\* cited by examiner

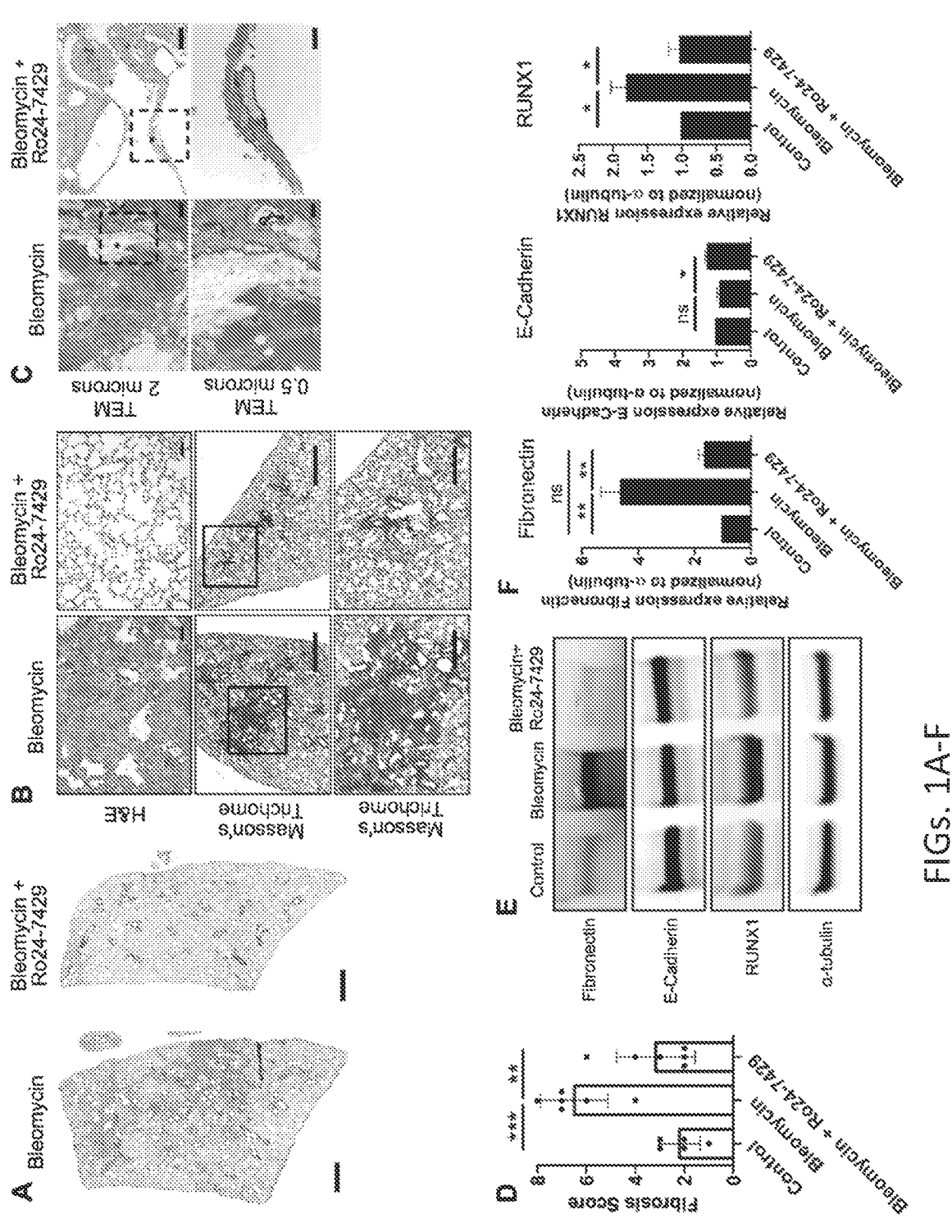
FIGS. 1A-F

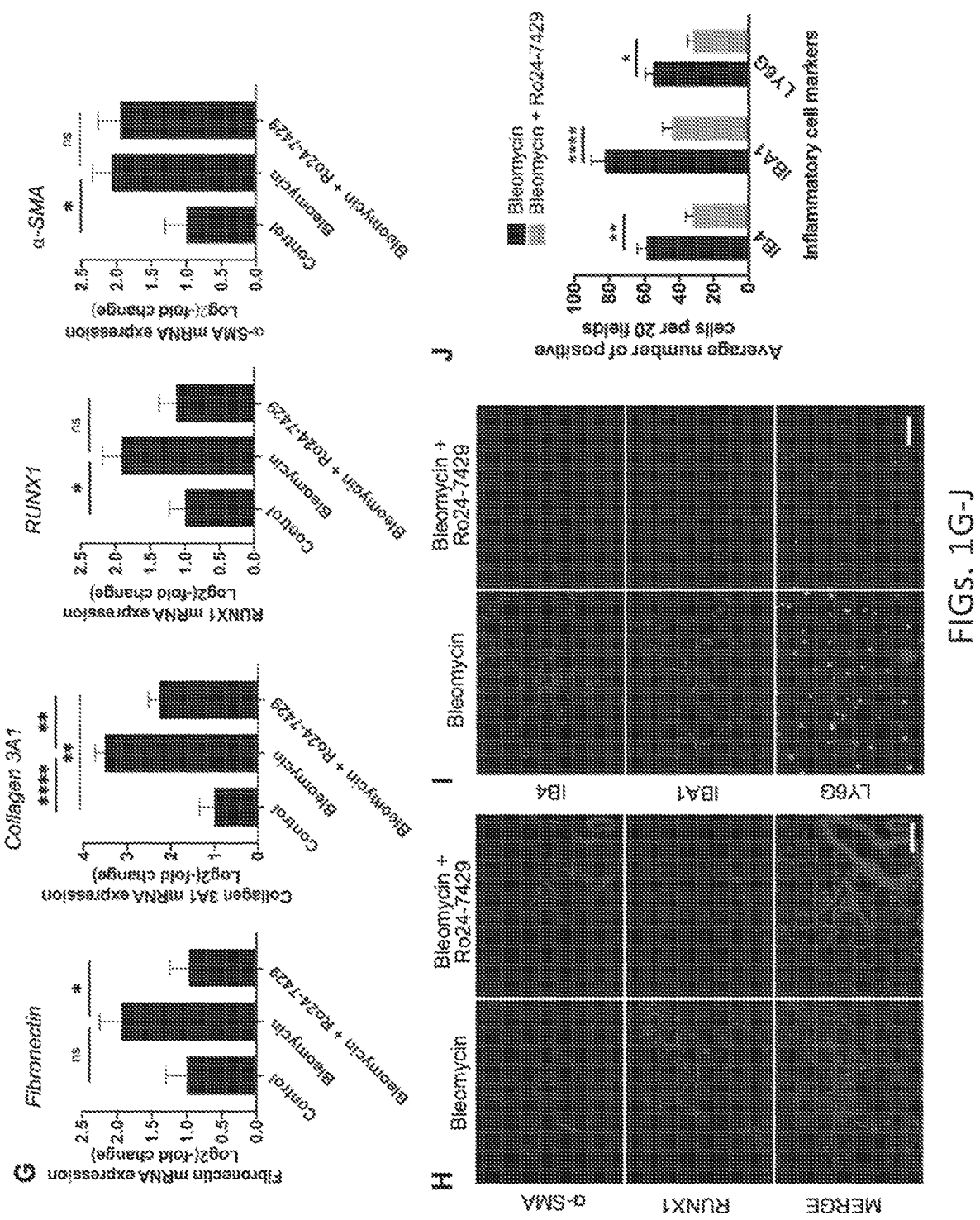
FIGS. 1G-J

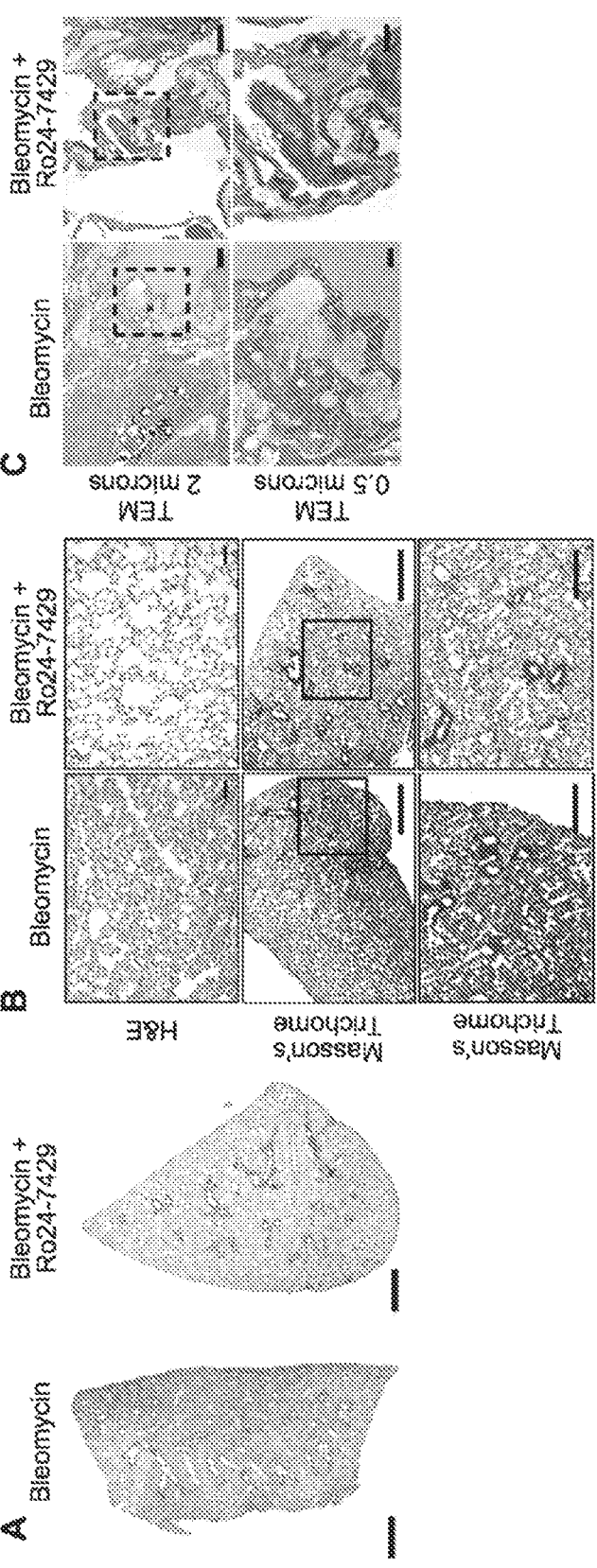
FIGs. 2A-C

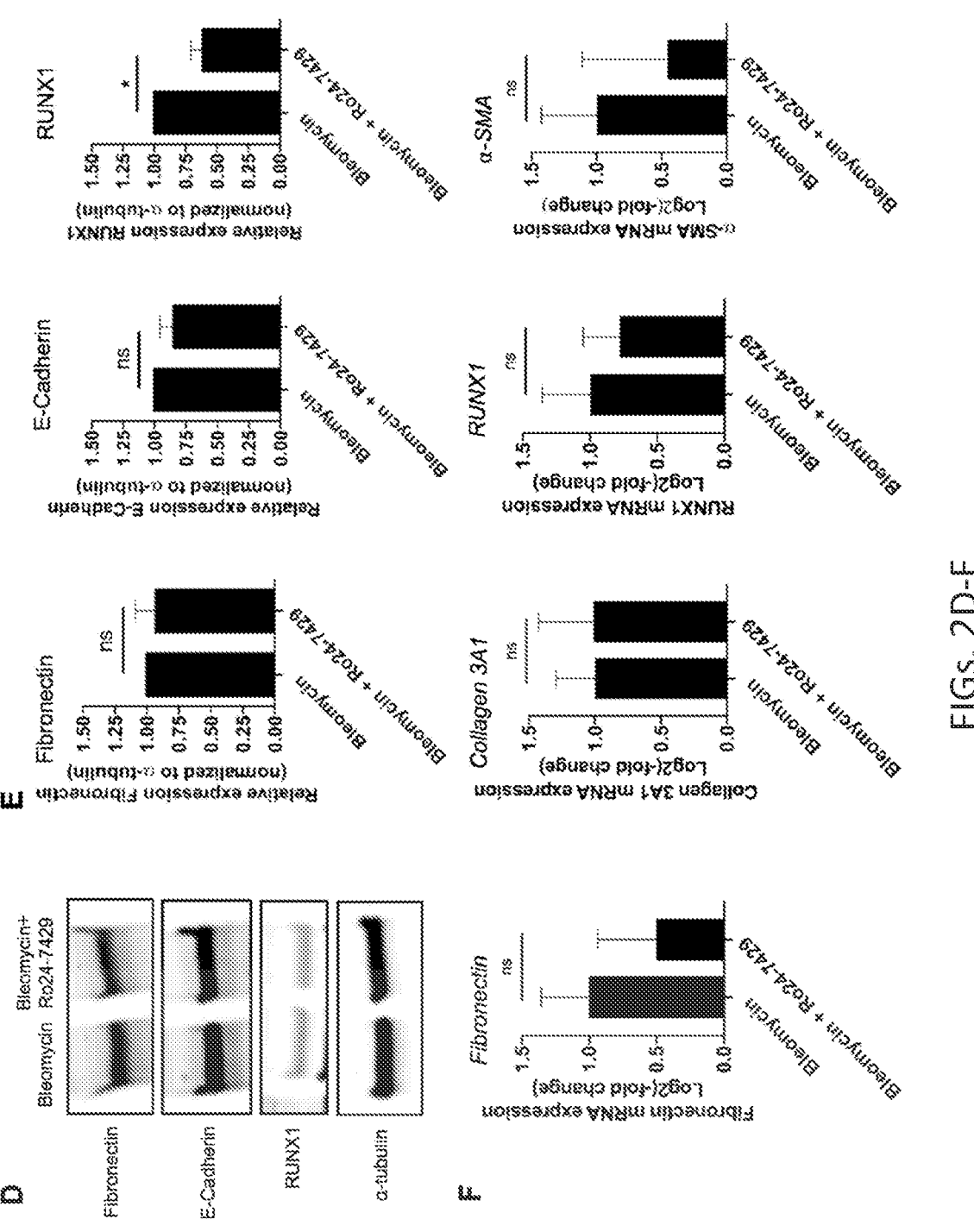
FIGs. 2D-F

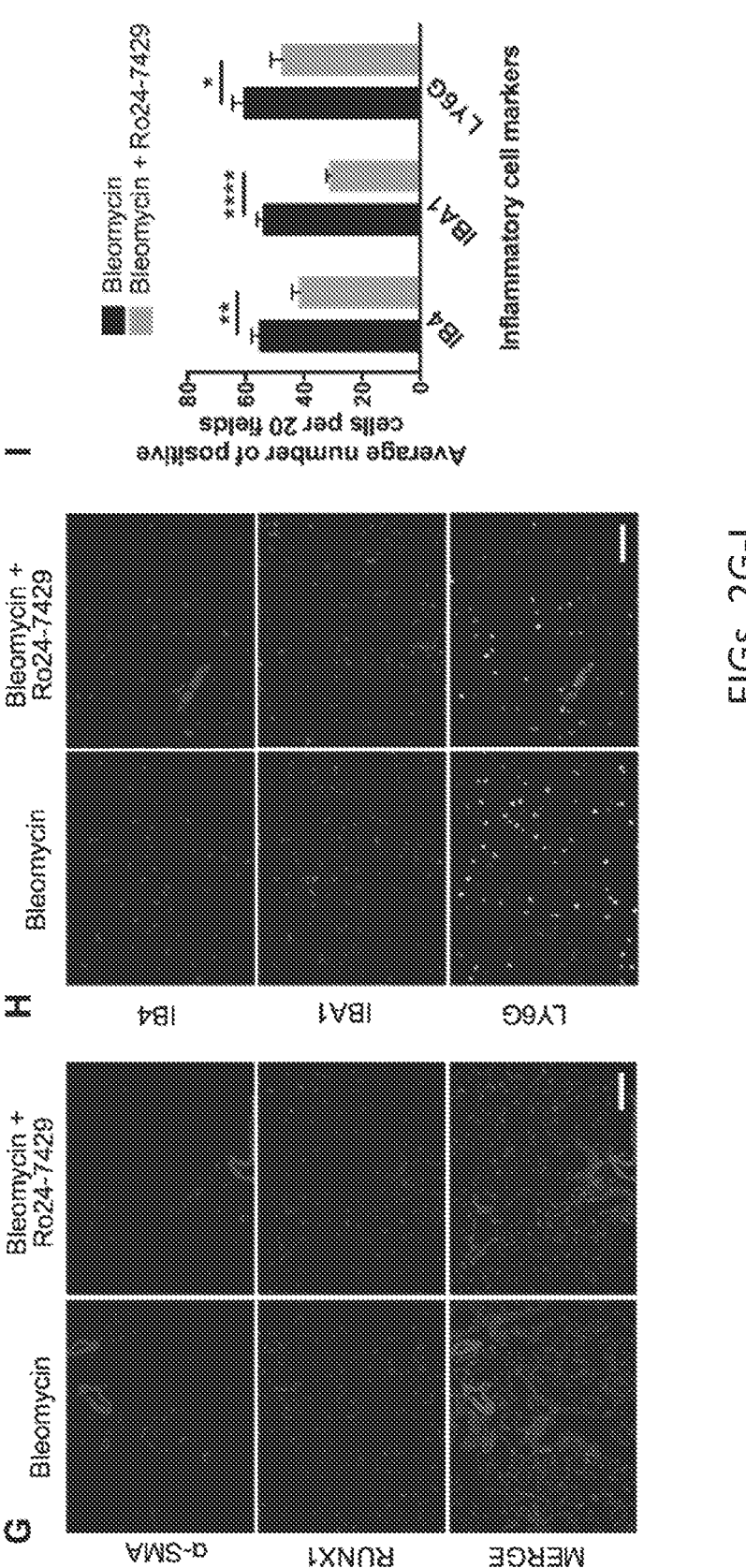
FIGs. 2G-I

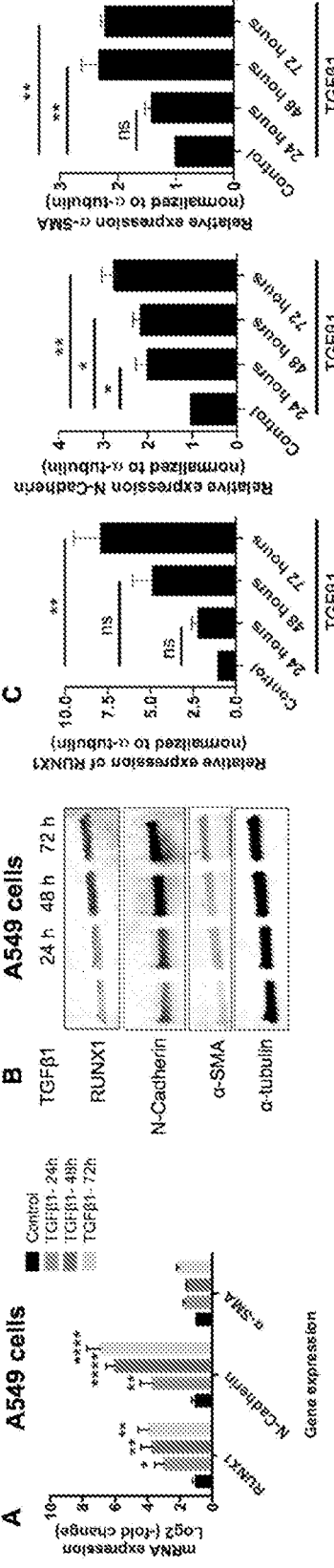
FIGs. 3A-C

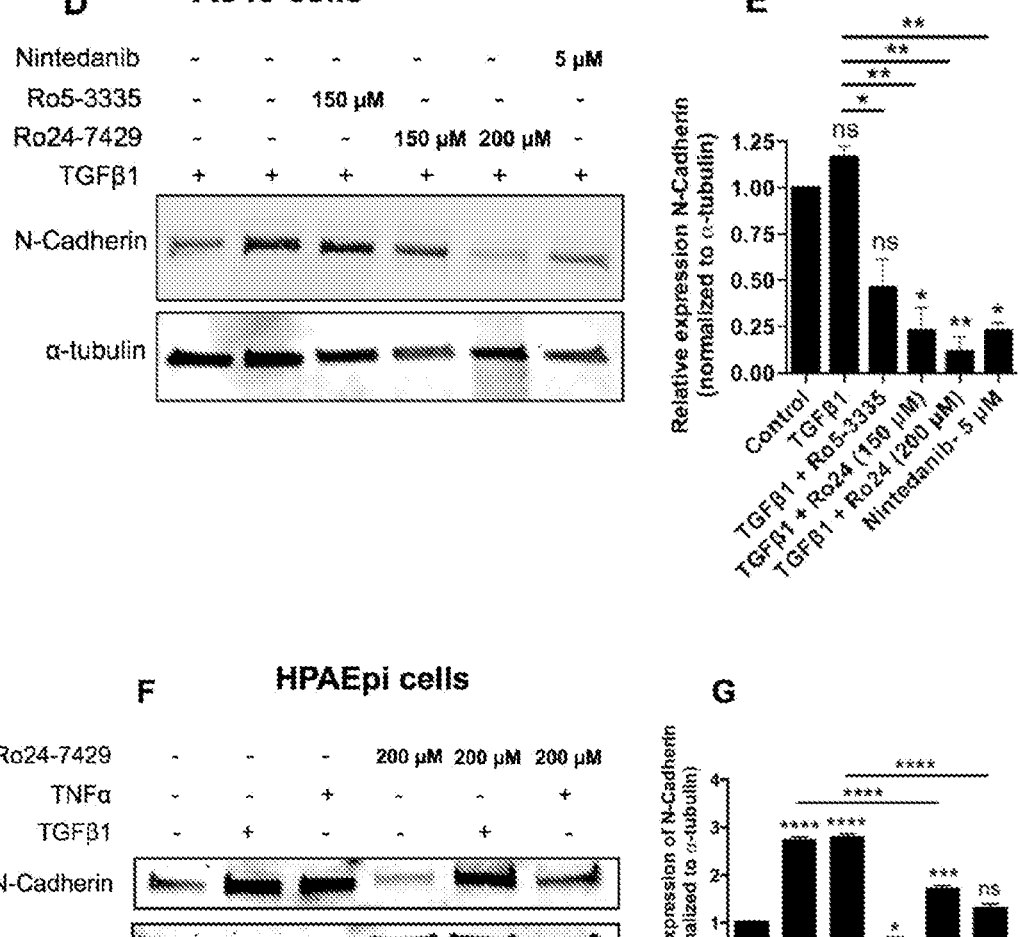
FIGs. 3D-G

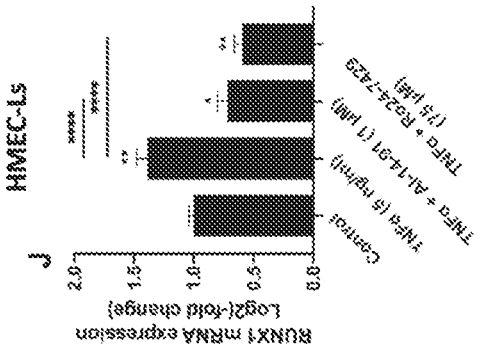
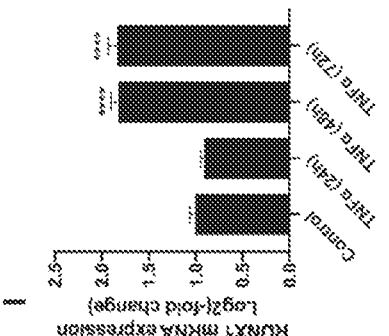
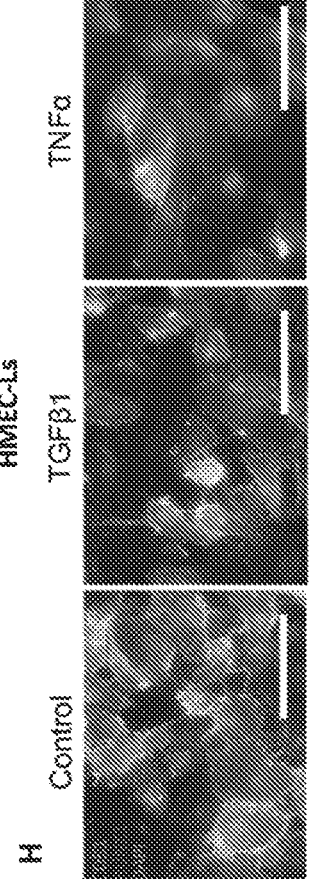
FIGs. 3H-J

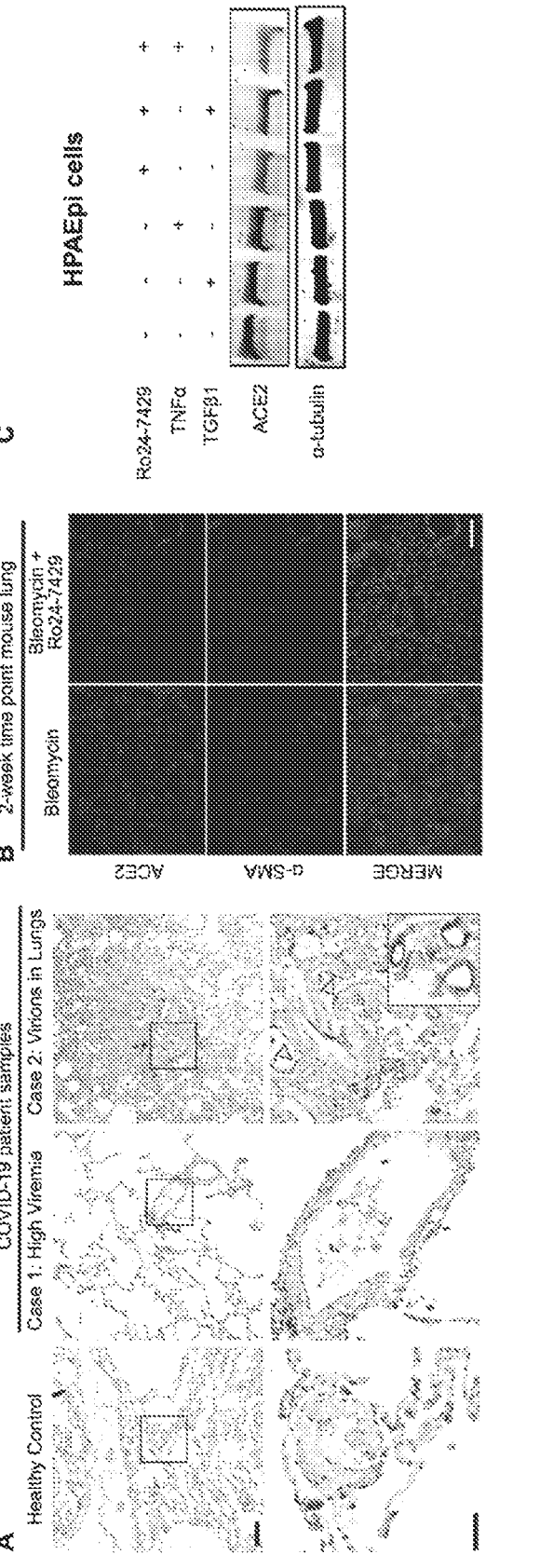
FIGs. 4A-C

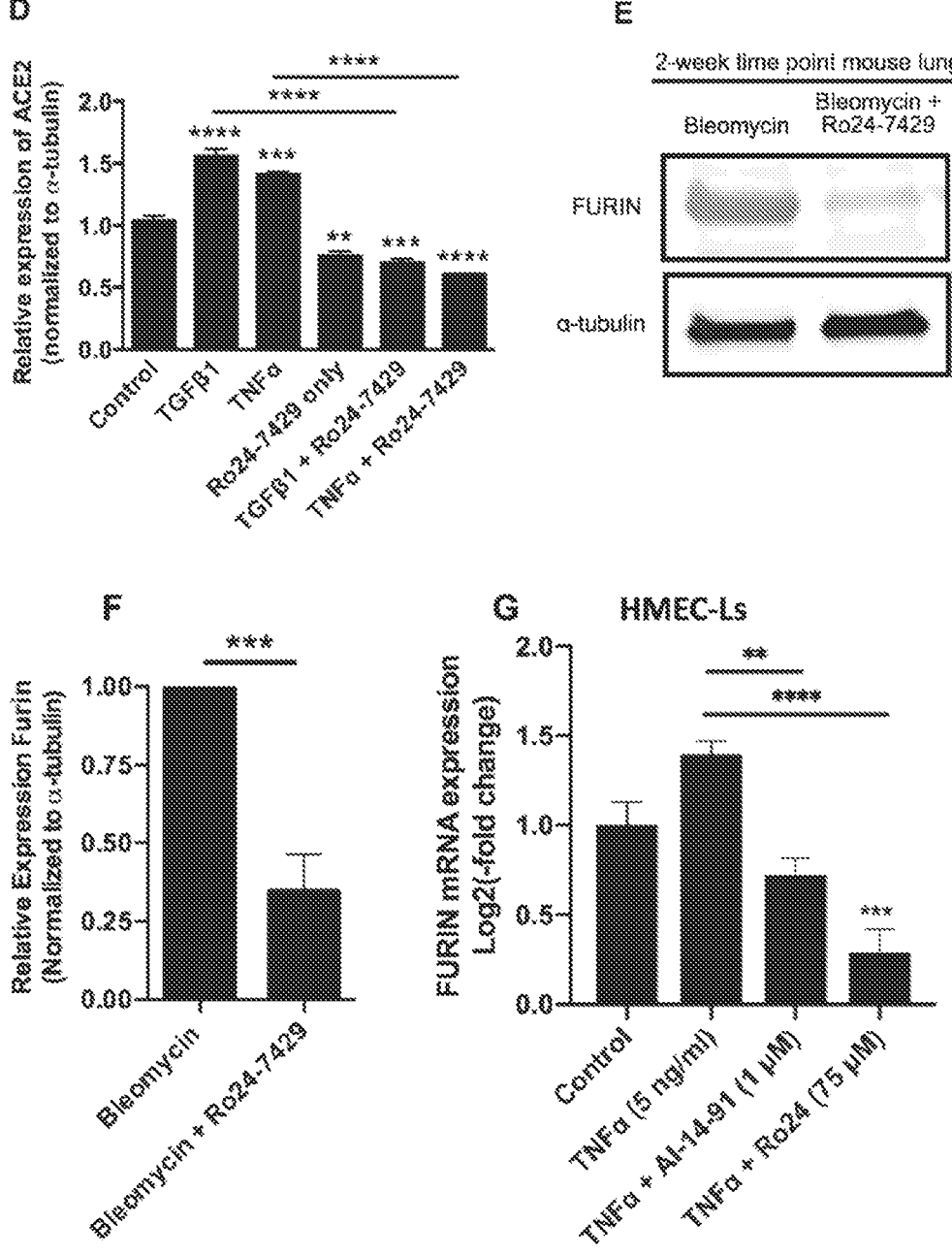
FIGs. 4D-G

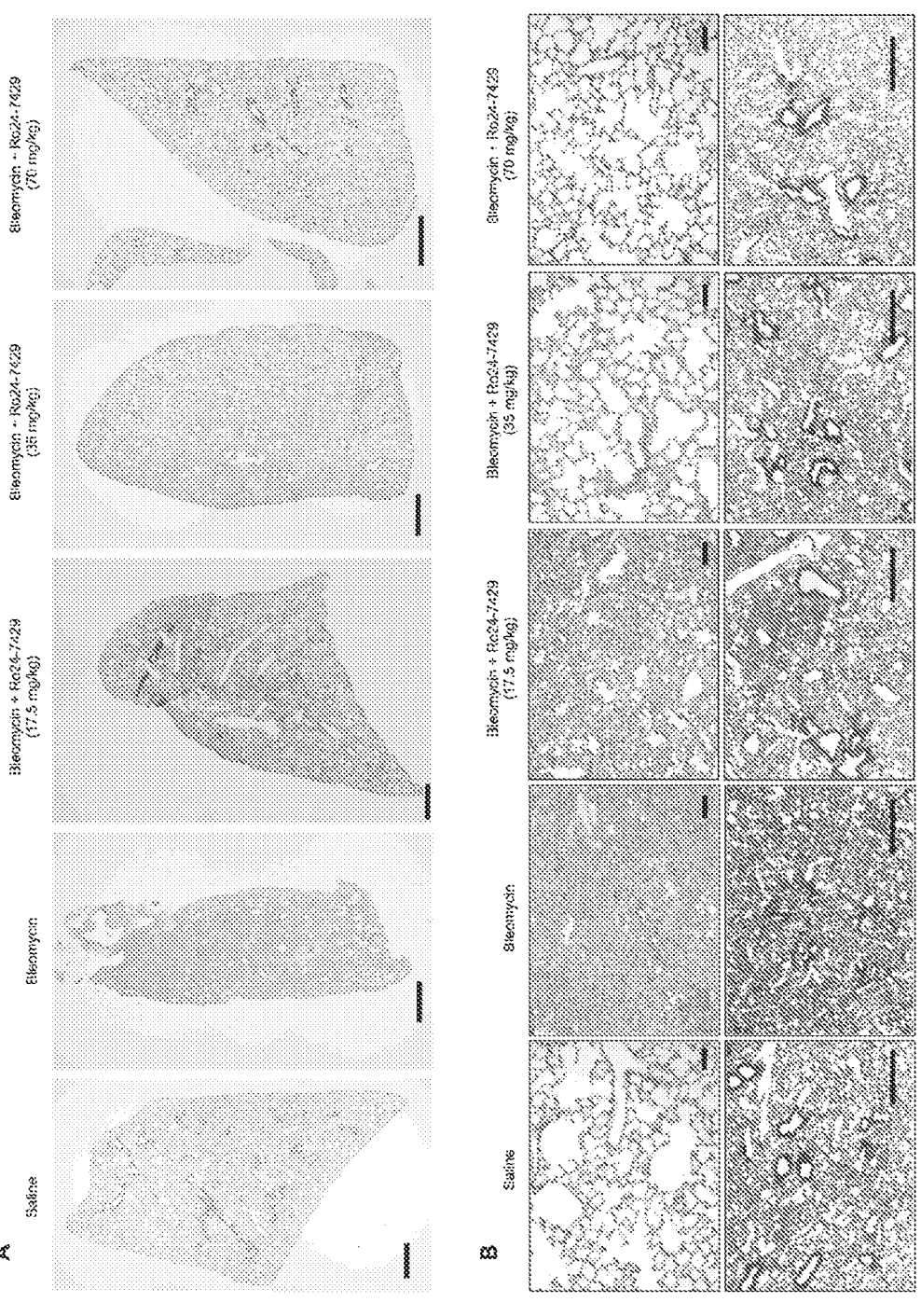
FIGs. 5A-B

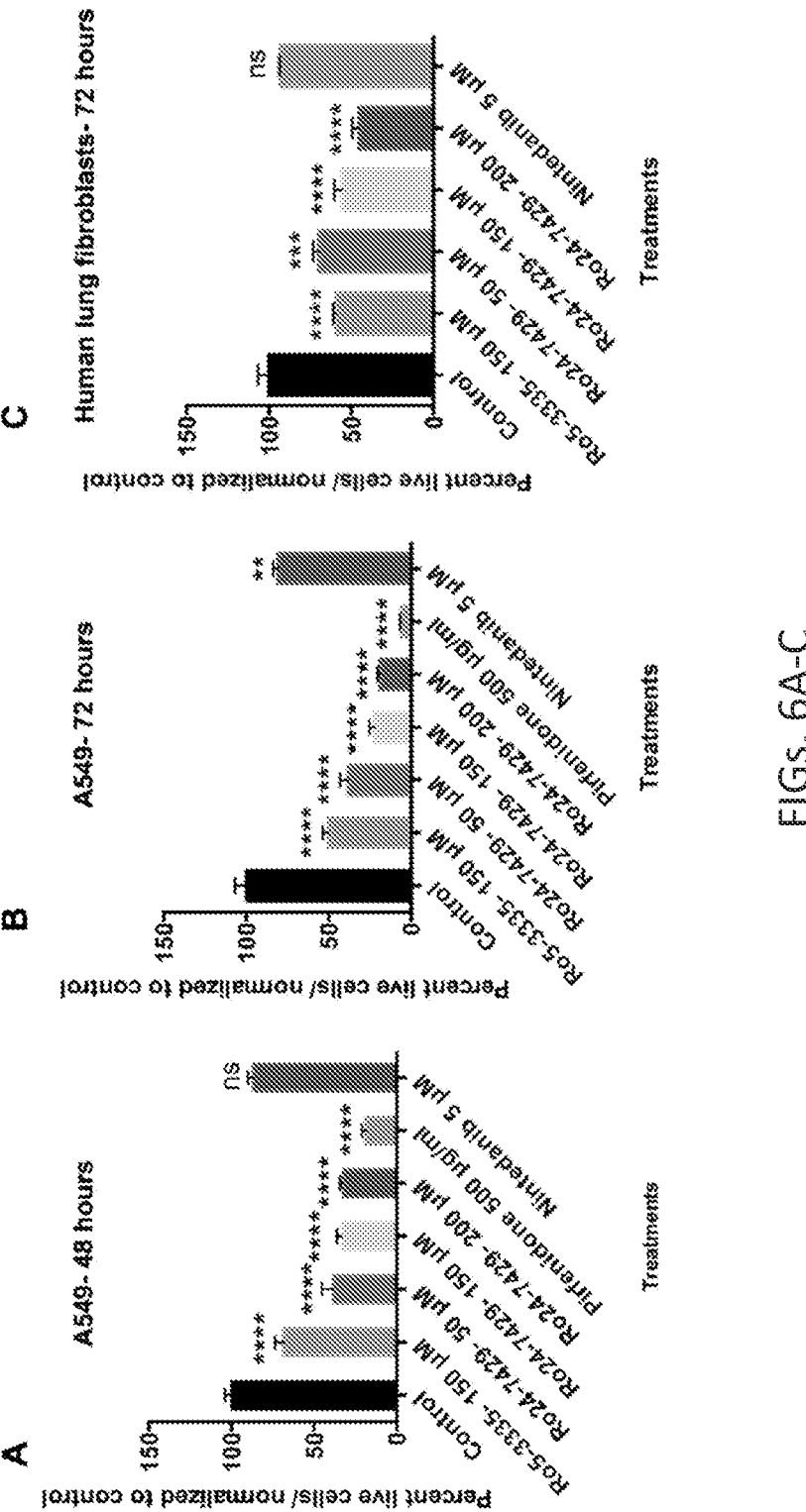
FIGs. 6A-C

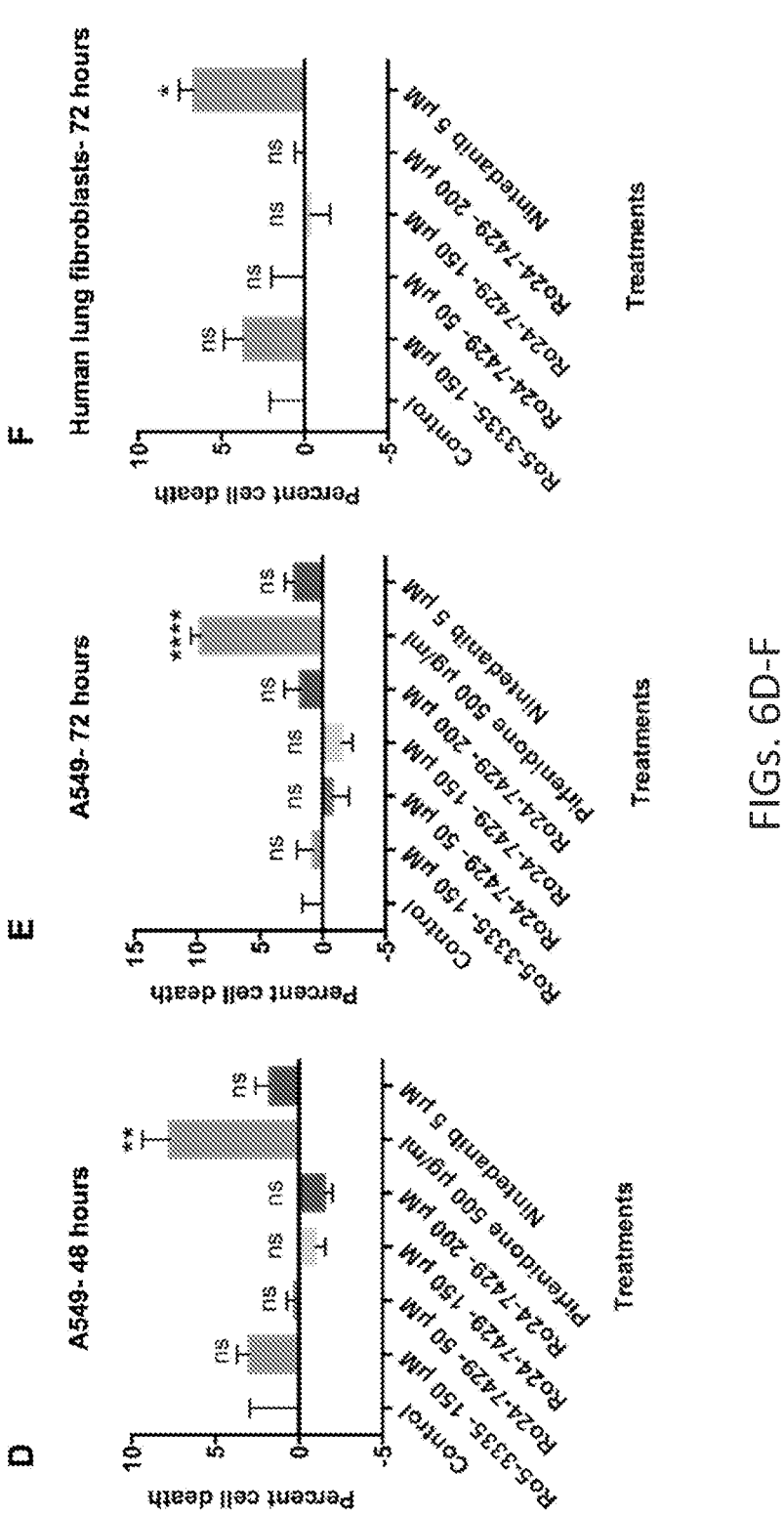
FIGS. 6D-F

FIG. 7

METHODS AND MATERIALS FOR TREATMENT OF FIBROSIS

CLAIM OF PRIORITY

This application is the national stage entry of International Patent Application No. PCT/US2021/027798, filed on Apr. 16, 2021, which claims the benefit of U.S. Provisional Patent Application Serial Nos. 63/014,194, filed on Apr. 23, 2020, and 63/129,418, filed on Dec. 22, 2020. The entire contents of the foregoing are hereby incorporated by reference.

STATEMENT OF FEDERALLY SPONSORED RESEARCH

This invention was made with government support under Grant No. W81XWH-17-2-0006 awarded by the Medical Research and Development Command. The government has certain rights in the invention.

SEQUENCE LISTING

This application contains a Sequence Listing that has been submitted electronically as an ASCII text file named 00633-0288US1_SL_ST25.txt. The ASCII text file, created on Oct. 21, 2022, is 5,487 kilobytes in size. The material in the ASCII text file is hereby incorporated by reference in its entirety.

TECHNICAL FIELD

Described herein are methods for treating and reducing risk of fibrosis, e.g., pulmonary fibrosis, in a subject by administering an inhibitor of runt-related transcription factor 1 (RUNX1) or core-binding factor subunit beta (CBFβ), e.g., in a subject who has a viral infection.

BACKGROUND

Pulmonary fibrosis is a chronic and often fatal lung disease characterized by the accumulation of extracellular matrix and the destruction of the lung parenchyma (1-3). The cause of pulmonary fibrosis is unknown in most cases, so is termed idiopathic pulmonary fibrosis (IPF). IPF is estimated to affect approximately 50 in 100,000 individuals, making IPF the most common interstitial lung disease in the US with a median survival of 3-5 years after diagnosis (4, 5).

SUMMARY

Provided herein are methods for treating or reducing risk of fibrosis in a subject. The methods include administering an effective amount of an inhibitor of runt-related family transcription factor 1 (RUNX1) or core-binding factor subunit beta (CBFβ). Also provided are compositions comprising an inhibitor of runt-related family transcription factor 1 (RUNX1) or core-binding factor subunit beta (CBFβ), for use in a method for treating or reducing risk of fibrosis in a subject.

In some embodiments, the fibrosis is pulmonary fibrosis, kidney fibrosis, or liver fibrosis, or radiation-induced fibrosis. In some embodiments, the fibrosis is post-surgical adhesions. In some embodiments, the fibrosis is not ocular fibrosis.

In some embodiments, the subject has a viral, bacterial, or fungal infection, or has had a chemical chemical lung injury, such as from smoke, a chemical burn, thermal injury.

In some embodiments, the subject has a coronavirus infection or influenza. In some embodiments, the coronavirus infection is infection with SARS or SARS-CoV-2.

Also provided herein are methods for reducing the risk of infection, severity of infection, or risk or severity of post-viral inflammatory syndromes, with a virus that relies on Angiotensin-converting enzyme 2 (ACE2) and/or FURIN for internalization. The methods include administering an effective amount of an inhibitor of runt-related family transcription factor 1 (RUNX1) or core-binding factor subunit beta (CBFβ). In some embodiments, the viral infection is a coronavirus or influenza. In some embodiments, the coronavirus is SARS-CoV or SARS-CoV-2. Also provided are compositions comprising an inhibitor of runt-related family transcription factor 1 (RUNX1) or core-binding factor subunit beta (CBFβ), for use in a method for reducing the risk of infection, severity of infection, or risk or severity of post-viral inflammatory syndromes, with a virus that relies on Angiotensin-converting enzyme 2 (ACE2) and/or FURIN for internalization.

In some embodiments, the inhibitor of RUNX family transcription factor 1 (RUNX1) is a small molecule inhibitor.

In some embodiments, the small molecule inhibitor of RUNX1 is Ro24-7429 (3H-1,4-Benzodiazepin-2-amine, 7-chloro-N-methyl-5-(1H-pyrrol-2-yl)-); Ro5-3335 ([7-chloro-5-(2-pyrryl)-3H-1,4 benzodiazapin-2-(H)-one]), 3H-1,4-Benzodiazepin-2-amine, 7-fluoro-N-methyl-5-(1H-pyrrol-2-yl)-, 7-fluro-1,3-dihydro-5-(1H-pyrrol-2yl)-2H-1, 4-benzodiazepin-2-one, NSC140873, MLS000548294, MLS001048862, or NSC156594.

In some embodiments, the inhibitor of core-binding factor subunit beta (CBFβ) is a small molecule inhibitor. In some embodiments, the inhibitor of CBFβ is 2-pyridyl benzimidazole AI-4-57 or analog thereof, preferably wherein the analog of is AI-10-47; AI-10-104; AI-12-16; AI-14-55; AI-12-126; AI-14-91; AI-14-18; or AI-14-72.

In some embodiments, the inhibitor of RUNX1 or CBFβ is an inhibitory nucleic acid that are directed to RUNX1 or CBFP. In some embodiments, the inhibitory nucleic acid is an antisense oligonucleotide, siRNA compound, or locked nucleic acid (LNA).

In some embodiments, the inhibitor of RUNX1 is a fusion protein that inhibits RUNX1, preferably a fusion protein comprising CBFP, preferably CBFβ-MYH11 fusion.

In some embodiments, the fusion protein is administered as a protein or as a nucleic acid encoding the fusion protein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-J. Antifibrotic and anti-inflammatory effect of Ro24-7429 at day 14 in the bleomycin model of PF. A-B)

Figure 4H:
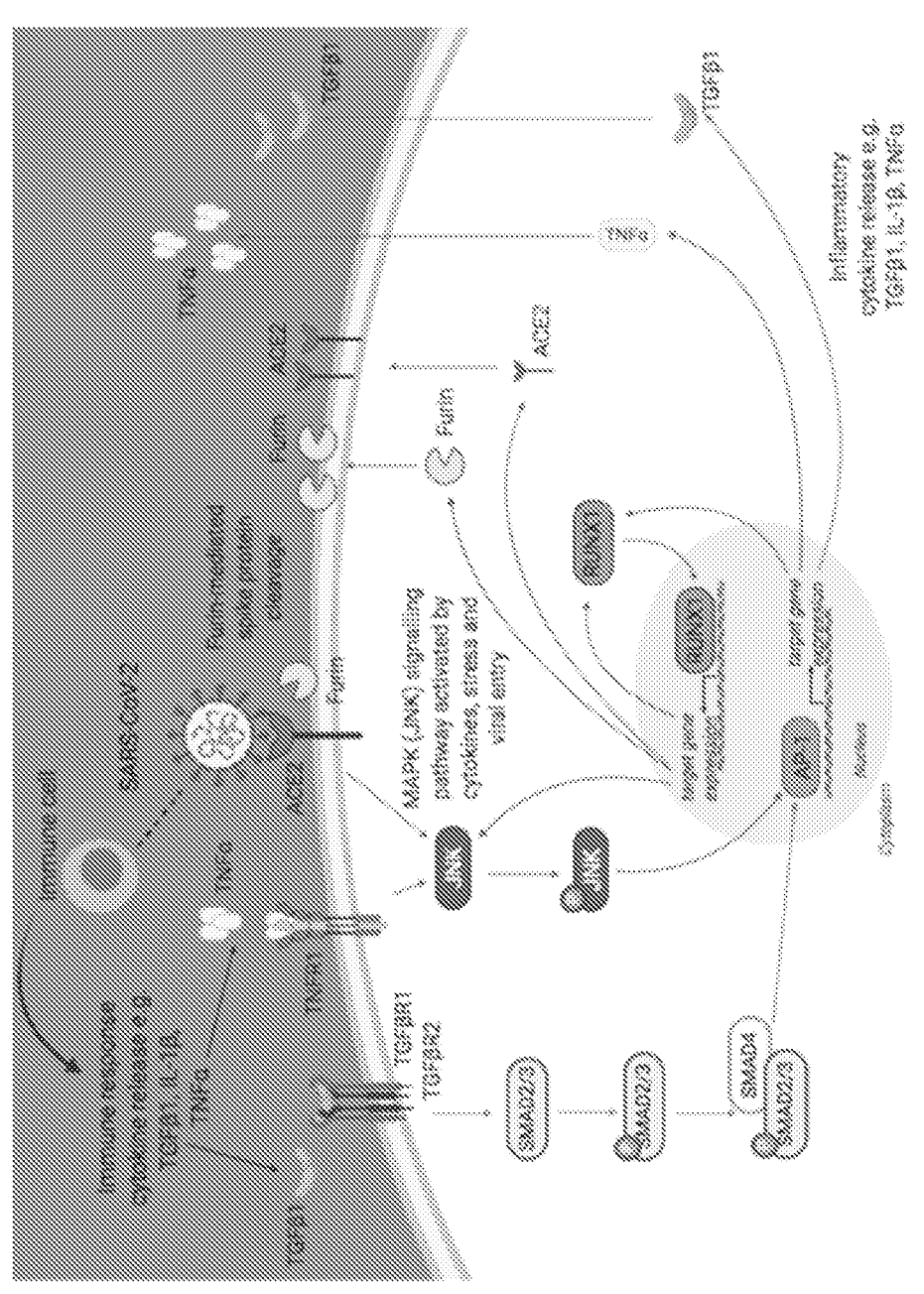

Histological images and collagen deposition of the lung tissue was assessed by H&E and Masson's trichrome staining and visualized using brightfield microscopy (Scale bars—50 μm and 1000 μm respectively). C) Representative TEM micrographs at low magnification (Scale bar—2 μm) and high magnification (Scale bar—500 μm) of bleomycin and Ro24-7429 treated lungs on day 14. D) Fibrosis score. E-F) Detection and quantification of RUNX1 and E-Cadherin and Fibronectin levels by Western blot in bleomycin and Ro24-7429 treated lungs. G) qRT-PCR analysis of mRNA levels of Fibronectin, Collagen 3A1, RUNX1, and α-SMA in bleomycin and Ro24-7429 treated lungs. H-I) Immunohistochemistry on paraffin sections for α-SMA, RUNX1, IBA1, IB4 and LY6G (Scale—100 μm). J) Quantification of IB4, IBA1 and LY6G positive cells in bleomycin and Ro24-7429 treated lungs. (All data are presented as mean±S.E.M, n=5-6, ns-not significant, *P<0.05, P<0.01, *P<0.001 and **** P<0.0001).

FIGS. 2A-I. Antifibrotic and anti-inflammatory effect of Ro24-7429 at day 7 in the bleomycin model of IPF. A-B) Histological images and collagen deposition of the lung tissue was assessed by H&E and Masson's trichrome staining and visualized using brightfield microscopy (Scale bars—50 μm and 1000 μm respectively). C) Representative TEM micrographs at low magnification (Scale bar—2 μm) and high magnification (Scale bar—500 μm) of bleomycin and Ro24-7429 treated lungs on day 14. D-E) Detection of Fibronectin, E-cadherin and RUNX1 levels by western blot in bleomycin (N=3) and Ro24-7429 (N=3) treated lungs. F) qPCR analysis of mRNA levels of Fibronectin, collagen 3A1, and RUNX1 and a-SMA in bleomycin (N=6) and Ro24-7429 (N=6) treated lungs. G-H) Immunohistochemistry on paraffin sections for α-SMA, RUNX1, IBA1, IB4 and LY6G (Scale—100 μm). I) Quantification of IB4, IBA1 and LY6G positive cells in bleomycin and Ro24-7429 treated lungs. All data are presented as mean±S.E.M, n=6, ns-not significant, *P<0.05, P<0.01, *P<0.001 and **** P<0.0001).

FIGS. 3A-J. The effect of cytokine stimulation and Ro24-7429 treatment on expression of fibrosis markers in lung epithelial and vascular endothelial cells. A) qRT-PCR analysis of mRNA levels of RUNX1, N-Cadherin and a-SMA after 24, 48 and 72 hours incubation with TGF-β1 in A549 cells. B) Western blot of RUNX1, N-Cadherin and α-SMA at 24, 48 and 72 hours treatment with TGF-β1 in A459 cells C) Quantification of Western blot for TGF-β1 time course in A549 cells. D-E) Western blot showing effect of Ro24-7429 on fibrotic marker N-cadherin after 72 hours treatment with TGF-β1 in A459 cells. F-G) Western blot of fibrotic marker N-cadherin in human alveolar epithelial cells (HPAEpi cells) stimulated with TGF-β1 or TNF-α with and without Ro24-7429 pretreatment. H) Representative images for HMEC-Ls fluorescently labeled with CD31 (Green) RUNX1 (Red) and DAPI (Blue) (Scale—100 μm). I) qRT-PCR analysis of mRNA levels of RUNX1 after 24, 48, and 72 hours treatment with TNF-α in HMEC-Ls cells. J) qRT-PCR of RUNX1 expression after pretreatment with AI-14-91 and Ro24-7429 with TNF-α treatment. (All data are presented as mean±S.E.M, n=3, ns-not significant, *P<0.05, P<0.01, *P<0.001 and **** P<0.0001).

FIGS. 4A-I. RUNX1 expression during SARS-CoV2 infection and the in vitro and in vivo effects of RUNX1 inhibition in human epithelial and endothelial cells. A) RUNX1 expression in human control lungs and two cases with SARS-CoV-2 with low (Case 1) or high abundance of viral proteins in lung (Cases 2) by immunostaining. Only Case 2 shows RUNX1 signal in vascular endothelia (yellow triangles) and capillaries (inset) (Scale Bars—100 μm). B) ACE2-α-SMA immunostaining at the 2-week time point. C-D) Western blot showing TGF-β1 and TNF-α induction of ACE2 with or without Ro24-7429 pretreatment. E-F) Western blot showing FURIN expression in bleomycin and Ro24-7429 treated lungs (N=5). G) qRT-PCR analysis of mRNA of FURIN after pretreatment with AI-14-91 or Ro24-7429 in the presence of TNF-α or in HMEC-Ls cells. H) Schematic of hypothesis of RUNX1 role in TGF-β1 (blue) and TNF-α (pink) signaling and its effects on SARS CoV-2 related proteins FURIN and ACE2. I) Pie chart showing the percentage distribution of SARS-CoV-2 related genes from oPOSSUM analysis with transcription factor binding sites (TFBSs) for RUNX1 (red), RUNX1 and AP-1 (orange), AP-1 (yellow), INK pathway genes (black), JNK pathway genes with AP-1 TFBSs (pink) and INK pathway genes with AP-1 and RUNX1 TFBSs (purple) and Other (grey) SARS-CoV-2 genes which do not have RUNX1 or AP-1 TFBSs. All data are presented as mean±S.E.M, n=5-6, (ns-not significant, *P<0.05, P<0.01, *P<0.001 and **** P<0.0001).

FIGS. 5A-B. Anti-fibrotic dose response comparison of intraperitoneal injection of Ro24-7429. A-B) Histological images and collagen deposition of the lung tissue was assessed by H&E and Masson's trichrome staining and visualized using brightfield microscopy (Scale bars—50 μm, 100 μm and 1000 μm respectively).

FIGS. 6A-F. CyQuant Cell Proliferation Assay and Lactate Dehydrogenase (LDH) assay 48 (6A, 6D) and 72 (6B, 6C, 6E, 6F) hours post treatment with RUNX1 inhibitor Ro5-3335 150 μM, increasing doses of Ro24-7429 (50 μM-200 μM), Pirfenidone 500 μg/ml, and Nintedanib 5 μM alone compared to vehicle treated showed a significant reduction in percent live cells at 48 hours and an even greater inhibition at 72 hours. RUNX1 Inhibition effectively inhibited the growth of A549 epithelial cells (6A, 6B, 6D, 6E) and human lung fibroblasts (HLF, 6C, 6F)). *P<0.05, P<0.01, *P<0.001, ****P<0.0001

Figure 7:
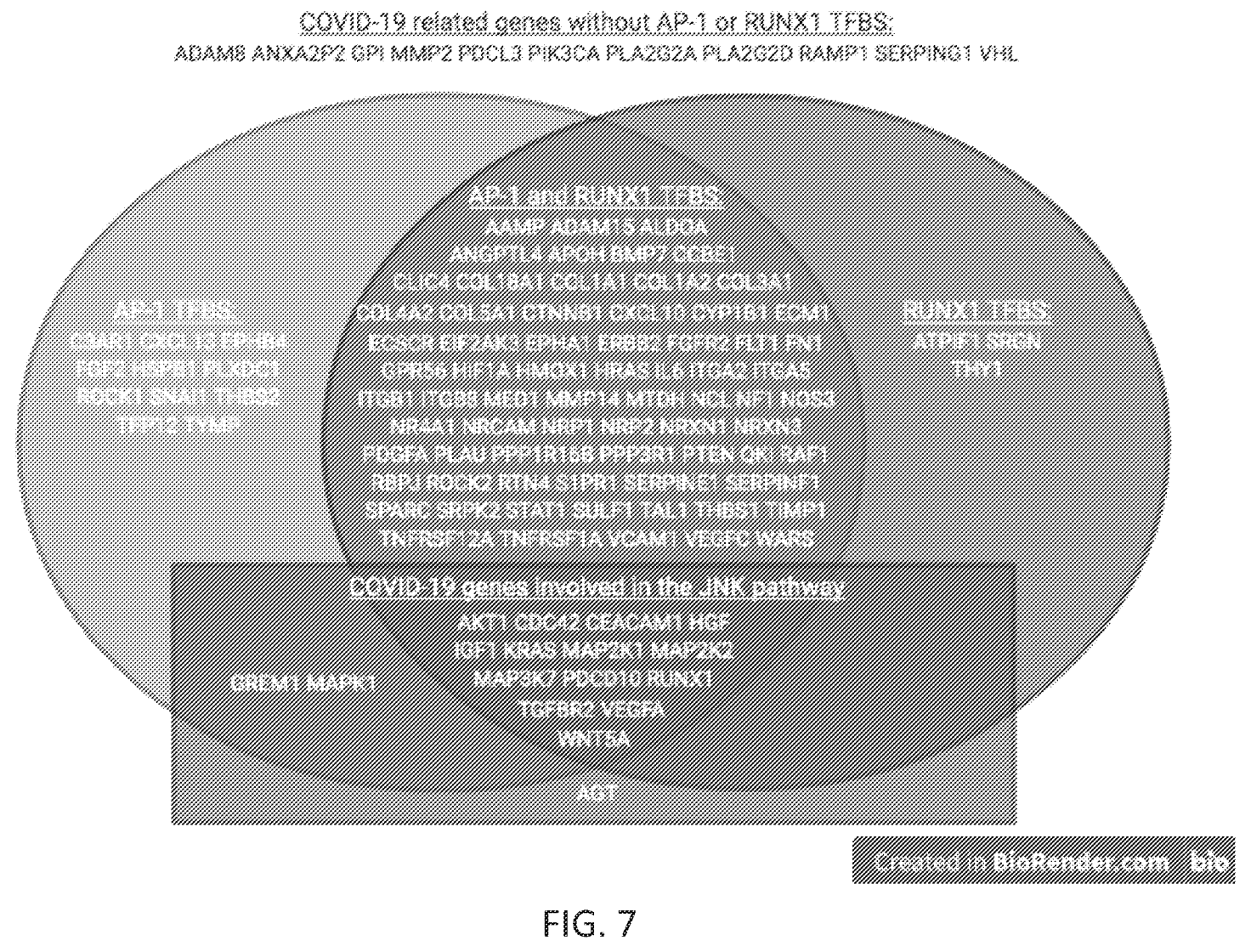

FIG. 7. oPOSSUM analysis of AP-1 and RUNX1 transcription factor binding sites (TFBS) in the context of COVID-19.

Figure 8:
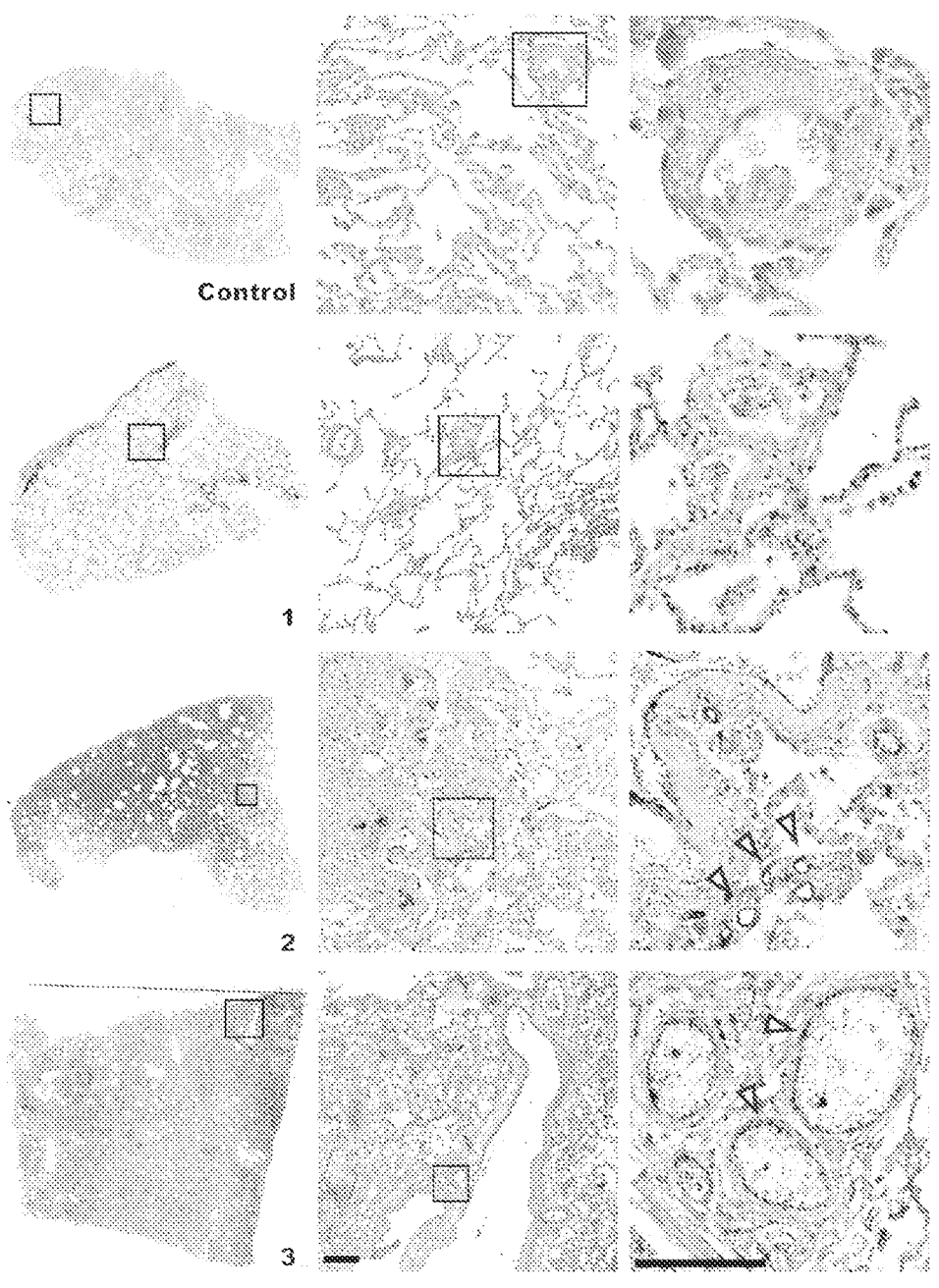

FIG. 8. RUNX1 immunostaining of postmortem human lung tissue from one control and three SARS-CoV-2 positive autopsy cases. Two cases show distinct positive signals in capillaries and vessel endothelia (yellow-red arrows).

Figure 9:
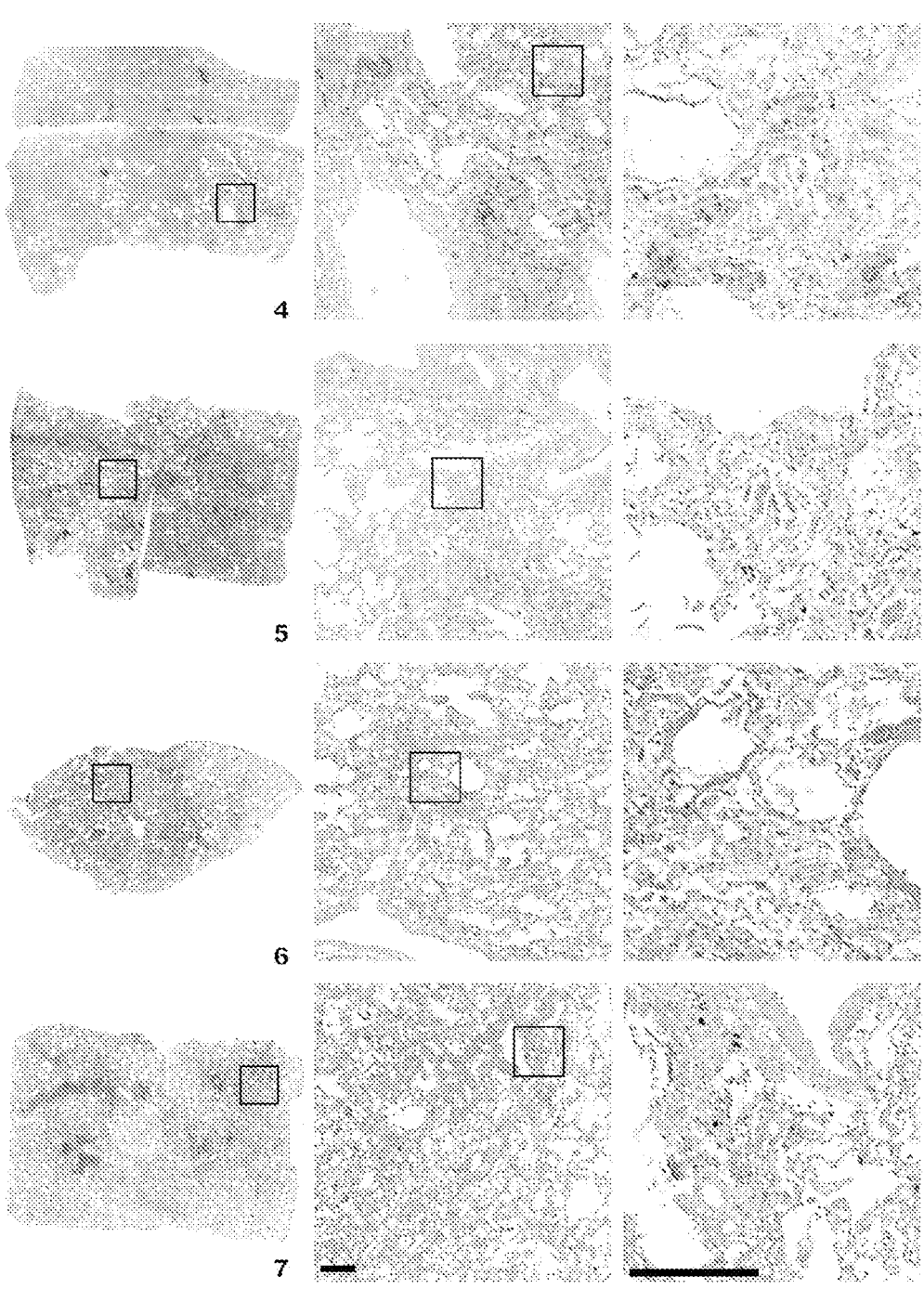

FIG. 9. RUNX1 immunostaining of human lung tissue from 4 SARS-CoV-2 positive cases. No positive signal is observed.

DETAILED DESCRIPTION

Despite recent developments in anti-fibrotic drugs such as nintedanib and pirfenidone, which slow IPF progression, there is still no widely accepted treatment that can reduce mortality in IPF (6). There is a dire need to identify therapeutics that modulate key targets in the pathological mechanisms of lung fibrosis. The repurposing of existing therapeutics with strong safety profiles may provide an accelerated path to identifying much-needed treatments as the incidence of IPF is rising (7, 8).

RUNX1 is a transcription factor critical for the process of regulating the differentiation of hematopoietic stem cells during development (20). RUNX1 functions as the α-DNA-binding component of the transcription factor core-binding factor (CBF) in association with CBFβ (21). While RUNX1 is recurrently mutated in sporadic myelodysplastic syndrome and leukemia, CBFβ mutations are found in 10-15% of adult de novo acute myeloid leukemia (AML) cases. These links to cancer have generated interest in the discovery and characterization of small molecule modulators of RUNX1 function, though to date none have been approved for clinical use (22, 23). RUNX1 functions in TNF-α-driven proliferation and migration of vascular endothelial cells, driving aberrant angiogenesis in a VEGF-independent pathway (24, 25). RUNX1 also functions as a master regulator of epithelial to mesenchymal transition (EMT) via TGF-02 signaling, suppressing epithelial phenotypes and promoting mesenchymal transformation in a blinding condition associated with ocular fibrosis called proliferative vitreo-retinopathy (26). These results suggest that RUNX1 activity is associated with both pathological angiogenesis and fibrosis, key cellular processes found in response to a number of diseases. Thus, RUNX1 modulation may result in novel modalities of treatment for prevalent, non-neoplastic conditions (24).

Ro24-7429 and Ro5-3335 are small molecule inhibitors of RUNX1 activity. Ro5-3335 has been widely used in multiple studies as a RUNX1 inhibitor and is commercially available (22). Ro24-7429 was originally developed for its potential effect as a Tat antagonist, and was tested in a phase 2 clinical trial in the treatment of acquired immunodeficiency syndrome (AIDS) in patients infected with human immunodeficiency virus (HIV) (27). Ro24-7429 had an acceptable safety profile in those clinical trials but was found to have no detectable antiviral activity (28). This study evaluated the role of RUNX1 in lung fibrosis and tested the potential antifibrotic effects of Ro24-7429 using the bleomycin-induced model of lung injury (29).

The present study demonstrates pre-clinical efficacy of RUNX1 inhibition using the small molecule Ro24-7429 in the bleomycin model of PF. The Ro24-7429 dose used here is equivalent to dosages previously tested in phase 1/2 trials that had a strong safety profile (28). Pretreatment with Ro24-7429 significantly reduced fibrosis and maintained alveolar structure through the inhibition of RUNX1 activity.

Current drugs with anti-fibrotic activity such as nintedanib and pirfenidone have been found to slow IPF progress (4). Without wishing to be bound by theory, the present data indicate that RUNX1 inhibition may operate via multiple pathways impacting different stages of PF progression resulting in a robust prevention of fibrosis. The present results demonstrated in vitro and in vivo that RUNX1 inhibition prevents pathological changes in the presence of TGF-β1 and TNF-α in human alveolar epithelial cells and human vascular endothelial cells respectively. Cytokine signaling caused by immune cell activation, cellular damage and inflammation activates downstream pathways including the INK pathway in endothelial cells and the SMAD pathway in lung epithelial cells (24, 44, 45). Both the INK and SMAD pathways converge on AP-1, as each is capable of activating/phosphorylating c-Jun, which dimerizes with c-Fos to form AP-1. AP-1 is known to cause the further production of inflammatory cytokines and is also linked to RUNX1 expression (FIG. 4H) (24, 46). These data clarify the role of cytokine signaling in mediating convergent RUNX1 activity in the bleomycin induced model of IPF in multiple cell types.

Previous studies evaluating the role of RUNX1 in lung epithelium have shown increased RUNX1 expression in lung tissue in response to acute lung injury via lipopolysaccharide (LPS) exposure (47). However, conditional knockout of RUNX1 within the lung epithelium increased susceptibility of acute lung injury to LPS via activation of NF-kB (48). The present work shows that pharmacological inhibition of RUNX1 inhibition via Ro24-7429 inhibited inflammation in adult tissues. Without wishing to be bound by theory, the present results suggest that pharmacological inhibition may allow for normal baseline RUNX1 activity, while inhibiting aberrant activity of RUNX1. It is also possible that the developmental transcriptional targets of RUNX1 may be different than the transcriptional targets in adult tissues. Further, in some embodiments the present methods can include inhibiting RUNX1 systemically, allowing for inhibition within multiple cell types beyond epithelium including fibroblasts, vascular endothelium, and inflammatory cells.

Ro24-7429 has also been investigated as a Tat antagonist (27, 28). To rule out off-target effects AI-14-91, a validated RUNX1 inhibitor, was also tested in the HMEC-Ls. Ro24-7429 caused a reduction in fibrotic makers, a phenotype also reported in studies that inhibited RUNX1 through molecular approaches (3).

Inflammatory Mediators of Fibrosis—TGF-β1, TNF-α, and FURIN

TGF-β1 is a critical mediator of pulmonary fibrosis and its expression is augmented in animal models of lung fibrosis and in human lungs with IPF (30, 32), in liver fibrosis (56), in fibrosis induced after radiation exposure (57), and surgical adhesions (58). TGF-β1 is involved in a range of cellular changes including proliferation, differentiation, apoptosis and death (33). TGF-β1 activation induces extracellular matrix production, and its effects are mediated through the SMAD2/3 pathway as illustrated through SMAD3 knockout that was found to prevent fibrosis in the bleomycin mouse model (34). Recent publications have highlighted the role of TGF-β1/SMAD/RUNX1 signaling in IPF (3). There has been growing interest in the role of RUNX1 in fibrosis in various organ systems including renal tubular epithelial cells in which RUNX1 was found to regulate markers of EMT and knockout of RUNX1 prevented kidney fibrosis (35). RUNX1 has been suggested to have a role in fibroblast activation and proliferation (36). RUNX1 is highly expressed in lipofibroblasts that are believed to be a source of myofibroblasts that contribute to IPF (37). Activation of fibroblasts and myofibroblasts results in an excessive deposition of extracellular matrix (ECM) proteins, an important pathogenic event that impairs lung function (38).

TNF-α is considered to be pro-angiogenic in vivo and elevated levels of TNF-α are implicated in several respiratory diseases including asthma, chronic obstructive pulmonary disorder (COPD) and acute respiratory distress syndrome (ARDS) (39-42). Importantly, TNF-α expression directly is correlated with increased endothelial permeability (43). In vascular endothelial cells, TNF-α signals to RUNX1 through a JNK pathway feedback loop (24). Specifically, in the lung, inhibition of TNF-α signaling has been shown to reduce collagen deposition, and additionally regulate the expression of the profibrotic mediator TGF-β1 (31, 41).

In conclusion, the present data indicate that RUNX1 is involved in multiple steps of the pathobiology of pulmonary fibrosis and RUNX1 inhibition may lead to an effective new therapy for PF of multiple etiologies. Thus RUNX1 inhibitors such as Ro24-7429 can be used for the treatment of fibrosis, including PF in lung, as well as fibrosis in other organs including kidney and liver; in fibrosis induced after radiation exposure; and surgical adhesions. Thus RUNX1 inhibitors can be used for the treatment of inflammatory conditions of the lung, including chronic obstructive pulmonary disease (COPD), acute respiratory distress syndrome (ARDS), and asthma, and in other organs.

SARS-CoV-2

The recent SARS-CoV-2 pandemic has the potential to cause a surge of post viral-infection induced cases of PF worldwide (9-12). Critical pathophysiological mechanisms involved in lung pathology associated with SARS-CoV-2 infection include 1) diffuse alveolar damage (13, 14); 2) pulmonary fibrosis (10); 3) increased vascular leakage/permeability (pulmonary edema) and aberrant angiogenesis (15); and, 4) "cytokine storm" in which uncontrolled inflammation leads to the release of an inordinate load of multiple cytokines leading to morbidity and mortality in patients with COVID-19 (15, 16). Although remdesivir, dexamethasone, and anti-SARS-CoV-2 antibody cocktails have received emergency approvals for the treatment of COVID-19, there is a critical clinical need for new therapies that can be easily administered and significantly impact clinical outcomes (17-19). Therapies may also offer relief for different mutant versions of the virus as they become resistant to existing vaccines. As shown herein, RUNX1 localization and signal was increased in a subset of human lungs infected with SARS-CoV-2. RUNX1 nuclear localization, an indication of activity was observed. The present data suggests that RUNX1 transcriptional activity likely plays a critical role in the pathologic host response to SARS-CoV-2 infection regulating the epithelial, fibroblast, and endothelial cell response. The oPPOSUM analysis of transcription factor binding sites (TFBSs) in genes found to be dysregulated in patients with COVID-19 revealed that 78% of these genes contain RUNX1 TFBSs suggesting that RUNX1 has an important role in the pathobiology of COVID-19 (15). The present results demonstrate that Ro24-7429 can be used for the treatment of PF in patients with COVID-19.

ACE2 and FURIN are critical for SARS-CoV-2 virus uptake within host cells. FURIN is a ubiquitous proprotein convertase involved in the proteolytic processing of a wide range of precursor proteins and activates a number of factors that are believed to be important in IPF including TGF-β1 a major contributing factor to the fibrotic changes associated with IPF. Initially, TGF-β1 is produced as an inactive polypeptide that requires correct proteolytic cleavage for its activation. The TGF-β1 cleavage site consists of a R—H-R-R sequence similar to the proprotein convertase (PC) recognition motifs. Interestingly this cleavage site is correctly cleaved by FURIN, a member of the PC family (50, 51). However, TGF-β1 is also cleaved by a number of other factors including integrin αvβ6 and the serine protease plasmin (30).

A potential direct link between RUNX1 function and the expression of ACE2 and FURIN was evaluated using our bleomycin-induced lung injury model and TGFβ/TNF-α-stimulated lung epithelial and vascular endothelial cells in vitro. RUNX1 was recently predicted as one of several potential modulators of ACE2 and FURIN expression based on genomic-guided molecular maps of upstream regulatory elements (49). We report for the first time that RUNX1 expression directly correlated with ACE2 and FURIN expression levels both in vitro and in vivo.

This provides further evidence that Ro24-7429 can be used as a therapeutic in subjects with SARS-CoV2 as this may have multiple avenues of efficacy; RUNX1 upregulation was identified in lung tissue from postmortem lungs of COVID-19 patients (see Example 6 and ref. 15). FURIN is a critical enzyme involved in the cleavage of the spike protein S1/S2 to allow subsequent interaction with ACE2 and viral internalization and importantly Ro24-7429 could have the potential to prevent post-infection associated fibrosis. RUNX1 inhibition blunted the expression of ACE2 and FURIN in a mouse model of lung injury and in human epithelial and vascular endothelial cells in vitro (see Example 6), indicating that RUNX1 inhibition may reduce the risk of infection with SARS-CoV-2.

Methods of Treatment

The methods described herein include methods for the treatment of disorders associated with fibrosis. In some embodiments, the disorder is lung fibrosis, e.g., IPF; in some embodiments, the disorder is lung fibrosis secondary to infection with a bacterium or virus, e.g., a coronavirus, e.g., SARS2 or SARS-CoV-2, or influenza. In some embodiments, the disorder is kidney or liver fibrosis; fibrosis induced after radiation exposure; surgical adhesions; fibrosis induced after radiation exposure; and surgical adhesions. The methods can also be used for the treatment of inflammatory conditions of the lung, including chronic obstructive pulmonary disease (COPD), acute respiratory distress syndrome (ARDS), and asthma, and in other organs. In some embodiments, the subject has a chemical lung injury, such as from smoke, a chemical burn, or a thermal injury.

As used in this context, to "treat" means to ameliorate at least one symptom of the disorder. Administration of a therapeutically effective amount of a compound described herein for the treatment of a condition associated with fibrosis will result in decreased fibrosis. For example, lung fibrosis including fibrosis secondary to viral infection, e.g., coronavirus (e.g., SARS2 or COVID-19) or influenza, can result in a reduction in pulmonary function; thus, a treatment can result in increased pulmonary function and a return or approach to normal pulmonary function. Pulmonary function can be assessed, e.g., by blood oxygen saturation (normal is above 95%), spirometry, lack of need for ventilator support. Arterial blood gas parameters can also be assessed, e.g., Partial pressure of oxygen (PaO$_2$) (normal is 75-100 mmHg); partial pressure of carbon dioxide (PaCO$_2$) (normal is 38-42 mmHg); arterial blood pH (normal is 7.38-7.42); or oxygen saturation (SaO$_2$) (normal is 94-100%).

Pulmonary function tests can also be measured, e.g.,

| | |
|---|---|
| FEV$_1$ | 80% to 120% |
| FVC | 80% to 120% |
| Absolute FEV$_1$/FVC ratio | Within 5% of the predicted ratio |
| TLC | 80% to 120% |
| FRC | 75% to 120% |
| RV | 75% to 120% |
| DLCO | >60% to <120% |

DLCO = diffusing capacity of lung for carbon monoxide.
FVC—Forced vital capacity; the total volume of air that can be exhaled during a maximal forced expiration effort.
FEV1-Forced expiratory volume in one second; the volume of air exhaled in the first second under force after a maximal inhalation.
FEV1/FVC ratio—The percentage of the FVC expired in one second.
MVV—Maximal voluntary ventilation.
ERV—Expiratory reserve volume; the maximal volume of air exhaled from end-expiration.
IRV—Inspiratory reserve volume; the maximal volume of air inhaled from end-inspiration.
RV—Residual volume; the volume of air remaining in the lungs after a maximal exhalation.
VT—Tidal volume; the volume of air inhaled or exhaled during each respiratory cycle.

See, e.g., Barreiro et al., Am Fam Physician. 2004 Mar. 1; 69(5):1107-1115.

In some embodiments, the methods are used in subjects who have COVID-19, and can result in a reduction in recovery time or a decrease in risk or severity of post-viral pulmonary syndromes; treatment or improvement in pneumonia, or risk or severity of pneumonia-associated fibrosis, e.g., reduces vasogenic edema, vascular leakage, and/or angiogenesis in subjects with virally-induced pneumonia, e.g., pneumonia associated with COVID-19. In some embodiments, the methods are used to prevent (reduce the risk of) disease or progression of disease in individuals that are asymptomatic but have tested positive for SARS-CoV-2.

In addition, described herein are methods for reducing the risk of infection, severity of infection, or risk or severity of post-viral inflammatory syndromes, with a virus that relies on ACE2 for internalization, e.g., coronaviruses, e.g., SARS2 and SARS-CoV-2. See, e.g., Monteil et al., Cell. 2020 May 14; 181(4):905-913.e7.

Generally, the methods include administering a therapeutically effective amount of an inhibitor of RUNX1, or of CBFβ (the binding partner for RUNX1) as described herein, to a subject who is in need of, or who has been determined to be in need of, such treatment.

RUNX1/CBFβ Inhibitors

A number of RUNX1 inhibitors are known in the art, including small molecules such as Ro24-7429 (3H-1,4-Benzodiazepin-2-amine, 7-chloro-N-methyl-5-(1H-pyrrol-2-yl)-) and Ro5-3335 ([7-chloro-5-(2-pyrryl)-3H-1,4 benzo-diazapin-2-(H)-one]), as well as analogs of each, e.g., 3H-1, 4-Benzodiazepin-2-amine, 7-fluoro-N-methyl-5-(1H-pyrrol-2-yl)- and 7-fluro-1,3-dihydro-5-(1H-pyrrol-2yl)-2H-1,4-benzodiazepin-2-one (see WO2019099595), NSC140873, MLS000548294, MLS001048862, or NSC156594. See, e.g., WO2018093797, Cunningham et al. (2012) Proc Natl Acad Sci USA, 109(36): 14592-14597, and U.S. Patent Application Publication No. 2014/0004082, the entire contents of each of which are incorporated herein by reference. Additional examples of RUNX1 inhibitors are described in U.S. Pat. Nos. 5,641,773; 5,164,376; 5,141, 735; 5,041,438; 5,036,101; and 3,405,122, as well as U.S. Patent Application Publication No. 2014/0004082, the entire contents of each of which are hereby incorporated herein by reference.

A number of CBFβ inhibitors are known in the art, including small molecules such as 2-pyridyl benzimidazole AI-4-57 and analogs thereof, e.g., AI-10-47; AI-10-104; AI-12-16; AI-14-55; AI-12-126; AI-14-91; AI-14-18; or AI-14-72 (see Illendula et al., EBioMedicine. 2016 June; 8: 117-131); and those described in WO2018093797. The benzimidazole compounds are believed to bind to the CBFβ portion of the CBFβ-SMMHC fusion protein and inhibit its binding to the Runt domain of RUNX proteins.

Some fusions of RUNX1 or CBFβ to other proteins that result in the formation of dominant negative inhibitors can also be used, e.g., the fusion of a fragment of CBFβ to a fragment of Myosin 11 (Liu et al., Science. 1993 Aug. 20; 261(5124):1041-4) (CBFβ-My 11). These fusions can be administered as inhibitors of RUNX1 as proteins, or as DNA or RNA that encode these proteins.

Alternatively, the present methods can include the use of inhibitory nucleic acids that are directed to RUNX1 or CBFP. Inhibitory nucleic acids useful in the present methods and compositions include antisense oligonucleotides, ribozymes, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics that hybridize to at least a portion of the target nucleic acid and modulate its function (i.e., inhibit expression). In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

Exemplary sequences for human RUNX1 are as follows:

| Nucleic acid | Protein | Variant | Name |
|---|---|---|---|
| NM_ 001754.5 | NP_ 001745.2 | 1 | runt-related transcription factor 1 isoform AML1c |
| NM_ 001122607.2 | NP_ 001116079.1 | 2 | runt-related transcription factor 1 isoform AML1a |
| NM_ 001001890.3 | NP_ 001001890.1 | 3 | runt-related transcription factor 1 isoform AML1b |

Variant 1 represents the longest isoform (AML1c). Variant 2 differs in the 5' UTR and coding region compared to variant 1. The resulting isoform (AML1b) is shorter and has a distinct N-terminus compared to isoform AML1c. Variant 3 differs in the 5' UTR and coding region as well as the 3' UTR and coding region compared to variant 1. The resulting isoform (AML1a) is shorter and has distinct N- and C-termini compared to isoform AML1c.

Exemplary sequences for human CBFβ are as follows:

| Nucleic acid | Protein | Name |
|---|---|---|
| NM_022845.3 | NP_074036.1 | core-binding factor subunit beta isoform 1 |
| NM_001755.3 | NP_001746.1 | core-binding factor subunit beta isoform 2 |
| NM_ 001368707.1 | NP_ 001355636.1 | core-binding factor subunit beta isoform 3 |
| NM_ 001368708.1 | NP_ 001355637.1 | core-binding factor subunit beta isoform 4 |
| NM_ 001368709.1 | NP_ 001355638.1 | core-binding factor subunit beta isoform 5 |
| NM_ 001368710.1 | NP_ 001355639.1 | core-binding factor subunit beta isoform 6 |

Variant 1 encodes the longest isoform 1. Variant 2 uses an alternate splice site in the 3' coding region compared to variant 1, that causes a frameshift. The resulting isoform 2 is shorter and has a distinct C-terminus compared to isoform 1. Variants 3 and 4 encode isoforms that are the same length, but have distinct protein sequences. Variants 5 and 6 encode isoforms that are the same length, but have distinct protein sequences.

Pharmaceutical Compositions and Methods of Administration

The methods described herein include the use of pharmaceutical compositions comprising RUNX1 inhibitors as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., in embodiments where the so pirfenidone, nintenamib, tocilizumab, steroids (e.g., corticosteroids (e.g., prednisone)), remdesivir, convalestent plasma, monoclonal antibodies against SARS-CoV-2.

Pharmaceutical compositions are typically formulated to be compatible with its intended route of administration. Examples of routes of administration include parenteral, e.g., intravenous, intradermal, subcutaneous, oral, nasal (e.g., inhalation, e.g., via an inhaler), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798. Such methods including administration by inhalation may be particularly useful in reducing risk of a coronavirus infection by inhibiting the ability of the virus to enter cells of the respiratory system, although systemic methods can also be used.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194, 389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996). In some embodiments, the composition is a nano-emulsion, e.g., as described in WO2019099595.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Examples

The invention is further described in the following examples, which do not limit the scope of the invention described in the claims.

Materials and Methods

The following materials and methods were used in the Examples herein.

Materials:

Tumor Necrosis Factor alpha (TNF-α), Transforming Growth Factor beta 1 (TGβ1), were purchased from Pepro-Tech (Rocky Hill, NJ, USA). RUNX1 inhibitor Ro5-3335 was purchased from Millipore-Sigma (Burlington, MA, USA). We contracted the synthesis of Ro24-7429 as fee-for-service from MedKoo Biosciences, which confirmed the correct structure by $^1$H-NMR nuclear magnetic resonance (NMR) and mass spectrometry, and purity >99% by high-performance liquid chromatography (HPLC, data not shown). The remaining Ro24-7429 was received as a kind gift from Paul Liu. The CBFβ-RUNX1 protein-protein inter-action inhibitor, AI-14-91 was synthesized as described previously (19).

Methods:

Animal Model

Animal procedures were approved by the Institutional Animal Care and Use Committee (IACUC) of Massachu-setts Eye and Ear, and performed in accordance with the Association for Research in Vision and Ophthalmology Statement for the Use of Animals in Ophthalmic and Vision Research. C57BL/6J male and female mice of 6-8 weeks-old were purchased from Jackson Laboratories. For all proce-dures, mice were anesthetized by intraperitoneal injection of Ketamine/xylazine mixture (100/50 mg/Kg).

Experimental Design

Bleomycin sulphate (Sigma-Aldrich) was dissolved in sterile 0.9% saline and administered as a single dose of 0.05 units in a total volume of 50 µl in saline solution per animal intratracheally (IT). Control animals received 0.05 mL saline alone. A preventative regimen was chosen and each animal received either Ro24-7429 drug 70 mg/kg or vehicle every other day 7 days before the induction of the model and continued until the end of the experiment for 1 week or 2 weeks. All animals received intratracheal instillations of either bleomycin on day 0 as previously described (52-55). A separate experiment was performed with similar drug-vehicle treatments and IT saline instillation for controls. The surgeon performing IT instillations was masked to the identity of the treatment groups.

Morphological Examination

Lung samples were fixed in 10% neutral buffered forma-lin (Sigma, HT501128-4L), for 24 hours for histological analysis. Fixed lungs were paraffin embedded and sectioned (5 µm-thick) and stained with hematoxylin and eosin (H&E) to examine gross morphology and Masson's trichrome stain to visualize collagen deposition and examined by micros-copy. Lung fibrosis was measured using quantitative histol-ogy using the Ashcroft method of analysis. All measure-ments were performed by two independent graders in a blinded fashion. Images were acquired with the Nikon Eclipse E800 microscope with an Olympus DP70 Camera. Adjacent 2× images of the lung were stitched together using Adobe Photoshop CS6.

Immunofluorescence Analysis of Lung Tissue

Paraffin embedded sections were processed for immuno-fluorescence using the following antibodies: anti-RUNX1 (1:100; LS-B13948; Lifespan Biosciences, Seattle, WA), anti-human a-SMA antibody (1:200; NB500-170; Novus Biologicals, Ontario, Canada), anti-Iba1 antibody (1:100; ab5076; Abcam, Cambridge, United Kingdom), anti-Ly6g antibody (1:100; ab25377; Abcam, Cambridge, United Kingdom), and Isolectin GS-IB4 Alexa Fluoro 594 Conju-gate (1:250; 121413; Invitrogen, Carlsbad, CA). For heat-induced antigen retrieval the slides were boiled in 10 mM sodium citrate buffer (pH 6.0) and then maintained at a sub-boiling temperature (95-100° C.) for 20 minutes and subsequently cooled on the bench top for 30 minutes. Slides were washed with distilled water and permeabilized with 0.5% Triton X-100 in PBS for 5 minutes and blocked (10% goat serum in PBS) for 1 hour at RT. The primary antibody was prepared in antibody dilution buffer (5% goat serum) and samples were incubated overnight with the antibody solution at 4° C. Sections were washed with PBS and incubated with goat anti-rabbit Alexa Fluor 594 secondary antibody (1:500; A-11012; Invitrogen, Carlsbad, CA) for 2 hours at room temperature. Slides were mounted and visu-alized using Prolong Gold Antifade Reagent with DAPI (P36935, Invitrogen). Images were obtained using an EVOS FL automated stage live cell imaging system (Life Tech-nologies, Cambridge, MA).

Transmission Electron Microscopy (TEM) Methods:

Mouse lungs were perfused with saline and fixed with half strength Karnovsky's fixative (2% formaldehyde+2.5% glu-taraldehyde, in 0.1 M sodium cacodylate buffer, pH 7.4) for 24 hours under refrigeration. After fixation, samples were trimmed into 1 mm thick segments, rinsed with 0.1M sodium cacodylate buffer, post-fixed with 2% osmium tet-roxide in 0.1M sodium cacodylate buffer for 1.5 hours, en bloc stained with 2% gadolinium triacetate in 0.05M sodium maleate buffer, pH 6, for 30 minutes, then dehydrated with graded ethyl alcohol solutions, transitioned with propylene oxide and infiltrated in tEPON-812 epoxy resin (Tousimis, Rockville, Maryland, USA) utilizing an automated EMS Lynx 2 EM tissue processor (Electron Microscopy Sciences, Hatfield, Pennsylvania, USA). The processed samples were oriented into tEPON-812 epoxy resin inside flat molds and polymerized using a 60° C. oven. Semi-thin and ultrathin sections were obtained using a Leica UC7 ultramicrotome (Leica Microsystems, Buffalo Grove, Illinois, USA) and diamond knives (Diatome, Hatfield, Pennsylvania, USA). Semi-thin sections were cut at 1 µm thickness through different lobes stained with 1% toluidine blue in 1% sodium tetraborate aqueous solution for assessment by light micros-copy. Ultrathin sections on grids were stained with aqueous 2.5% gadolinium triacetate and modified Sato's lead citrate. Grids were imaged using a FEI Tecnai G2 Spirit transmis-sion electron microscope (FEI, Hillsboro, Oregon, USA) at 80 kV interfaced with an AMT XR41 digital CCD camera (Advanced Microscopy Techniques, Woburn, Massachu-setts, USA) for digital TIFF file image acquisition. TEM digital images were captured at 2 k×2 k pixel@16-bit resolution.

Cell Culture:

Human type II alveolar epithelial cells (A549) were a generous gift from Dr. Lagares (Mass General Hospital).

Cells were maintained in low glucose-DMEM containing 10% FBS, 2 mM L-glutamine, 100 U/ml penicillin and 100 μg/ml streptomycin at 37° C. in a humidified 5% C02 atmosphere. Confluent cultures of cells were pretreated with Ro24-7429 for 24 hours followed by stimulation with 5 ng/ml of TGF-β1.

Human Microvascular Endothelial Cells (Lung) (HMEC-Ls, CC-2527) purchased at P1 from Lonza (Basel, Switzerland) were incubated at 37° C. with 5% C02. HMEC-Ls were plated at P2-6 using endothelial growth media (EGM-2) (Lonza) supplemented with EGM™-2 MV Microvascular Endothelial Cell Growth Medium-2 BulletKit™ (CC-2527) Cells were treated at P3-7 in endothelial basal media (EBM-2) (Lonza) supplemented with 5% FBS, 1% gentamycin/amphotericin and selected stimulants.

Human Pulmonary Alveolar Epithelial cells (HPAEpiCs) were purchased from ScienCell (Carlsbad, CA, USA) and cultured in alveolar epithelial cell medium (ScienCell) supplemented with 2% fetal bovine serum (FBS), epithelial cell growth supplement, 100 U/mL penicillin G, and 100 g/mL streptomycin. The cells were cultured and maintained in 6-well plates for experimental purposes.

oPOSSUM Analysis:

Angiogenesis-associated genes in COVID-19 deceased patients were previously reported (15). Analysis of this gene versity Medical-Center of Hamburg-Eppendorf as described in previous works (55) between March and September 2020 in the dissection room with Institutional Review Board approval from the independent ethics committee of the Hamburg University (protocol-no PV7311). Seven COVID-19 patients and one case with negative PCR virus test were selected. Clinical data including pre-existing medical conditions, medical course prior to death and ante mortem diagnostic findings were assessed (Table 2). Lung tissue samples were formalin-fixed and paraffin-embedded (FFPE). Sample were immunohistochemically stained using a Ventana Benchmark XT Autostainer (Ventana, Tucson, AZ, USA). RUNX1 staining was performed in accordance with the manufacturer's recommendations, using a RUNX1 antibody (HPA004176; rabbit polyclonal, Sigma Aldrich, Hamburg, Germany; dilution 1:200). For detection of specific binding, the Ultra View Universal 3,3'-Diaminobenzidine (DAB) Detection Kit (Ventana, Roche) was used which contains secondary antibodies, DAB stain and counter staining reagent. Slides were examined and diagnosed by an experienced lung pathologist (SS). Whole slides were then electronically scanned at high magnification (x40) as high-resolution images (1900×1200 pixels) with a NanoZoomer 2.0-HT (Hamamatsu Photonics, Hamamatsu, Japan).

TABLE 2

| | | | | | | | |
|---|---|---|---|---|---|---|---|
| | | | | Patient demographics | | | |
| # | Sex | Age | Post-mortem Interval (days) | Place of Death | Cause of death | Comorbidities | Histology |
| 1 | M | 82 | 5 | Normal ward | Pneumonia with acute cardiac decompensation | Hypertension, COPD, diabetes, CHD | DAD, mostly emphysema |
| 2 (Case 1) | F | 84 | 4 | Own home | Lung embolism, pneumonia, myocardial infarction | Diabetes, cardiac insufficiency | Low DAD, RUNX1 signal |
| 3 (Case 2) | F | 75 | 2 | Own home | Lung embolism, pneumonia | CHD, hypertension | DAD, RUNX1 signal |
| 4 | M | 76 | 3 | ICU | Sepsis, pneumonia | Condition after C.a. Thyroid carcinoma, acute myeloid leukaemia, dilated cardiomyopathy | DAD |
| 5 | M | 81 | 1 | ICU | Lung embolism, pneumonia | Myelofibrosis, CHD, steatosis hepatis | DAD |
| 6 | F | 59 | 0 | ICU | Pneumonia | Multiple Myeloma | DAD |
| 7 | F | 83 | 2 | ICU | Pneumonia | Condition after lung embolism, Non-Hodgkin's-Lymphoma | DAD |

DAD = diffuse alveolar damage, CHD = coronary heart disease, COPD = chronic obstructive pulmonary disease, ICU = Intensive Care Unit.

set was performed using oPOSSUM (v.3.0), Human Single Site analysis tool with either RUNX1 or AP-1 as the JASPAR CORE transcription factor binding site (TFBS) profile. Conservation cutoff 0.4; matrix score threshold 85%; up/downstream sequence 5000. Target gene hits against AP-1 and RUNX1 were manually compared, while genes associated with the JNK pathway were manually matched with JNK signaling pathway genes reported by amigo.geneontology.org.

Human Tissue Immunohistochemistry:

All autopsies of SARS-CoV-2 infected deceased, were performed at the Institute of Legal Medicine, of the Uni- Western Blotting:

Protein concentration was determined by Pierce Bicinchonic acid (BCA) protein assay kit (ThermoFisher; 23227) according to the manufacturer's instructions. 20 μg of total cell lysates were prepared in 4 μL 1M 1,4-dithiothreitol (DTT; Sigma Aldrich) and 10 μL Laemmli buffer (Boston Bioproducts) to a final volume of 40 μL and denatured 5 min at 90° C. Samples were separated electrophoretically for 1 h at 70 V using 4-20% pre-cast gradient gels (Mini-PROTEAN TGX, Bio-Rad) and SDS-Tris-Glycine buffer (Bio-rad). Proteins were transferred to 0.45 μm nitrocellulose membranes for 1 h at 70 V in ice cold 2000 Methanol Tris-Glycine buffer (Bio-rad). Membranes were blocked for 1 h with Odyssey Blocking Buffer (LI-COR Biosciences). Then incubated with primary antibodies for 3 hours RT or overnight at 4 degrees celcius and then washed 3× with TBS-T and incubated with secondary antibodies IRDye 800CW donkey anti-mouse for 1 hour and washed 3× with TBS-T.

Immunoreactive bands were detected using the Odyssey Infrared Imaging System and visualized on the Image Studio software (version 2.1, LI-COR Biosciences).

Quantitative RT-PCR:

HMEC-Ls were plated and treated as described above for between 24 and 72 hours. The timepoint of qRT-PCR lysis collection when not specified is 48 hours of treatment. RNA was extracted using RNeasy Mini Kits (QIAGEN, Hilden, Germany) as per the manufacturer's instructions. Transcription into complementary DNA was performed using the iScript cDNA synthesis kit (Bio-Rad, Hercules, CA, USA), following the manufacturers protocol and probed using FastStart Universal SYBR Green Master Mix (Hoffmann-La Roche, Basel, Switzerland) in 384-well white plates.

Mice were treated as described previously before euthanasia. Lung samples were collected for qRT-PCR analysis and tissues lysed by homogenization. RNA was extracted using RNeasy Mini Kits (QIAGEN), as per the manufacturer's instructions for tissue samples. Transcription into complementary DNA and analysis were performed as stated previously. Primers for selected genes (Table 1) were purchased from Integrated DNA Technologies (Coralville, IA, USA).

TABLE 1

| | | Primer sequences used in qRT-PCR analysis | |
|---|---|---|---|
| Gene | Species | Forward | Reverse |
| HPRT1 | human | ACCCTTTCCAAATCCTCAGC | GTTATGGCGACCCGCAG |
| RUNX1 | human | TCCACAAACCCACCGCAAGT | CGCTCGGAAAAGGACAAGC |
| FURIN | human | TCGGGGACTATTACCACTTCTG | CCAGCCACTGTACTTGAGGC |
| ACE2 | human | ACAGTCCACACTTGCCCAAAT | TGAGAGCACTGAAGACCCATT |
| HPRT1 | mouse | TCAGTCAACGGGGGACATAAA | GGGGCTGTACTGCTTAACCAG |
| RUNX1 | mouse | TGGTGGAGGTACTAGCTGACC | CGAGTAGTTTTCATCGTTGCCTG |
| FURIN | mouse | AGGGACGTGTATCAGGAGCC | CCTGCTAGGTCGGGATGATTC |
| ACE2 | mouse | GGCGACAAGCACAGACTACAA | GCCATCTCGTTTTTCAGGACC |
| α-SMA | mouse | GTCCCAGACATCAGGGAGTAA | TCGGATACTTCAGCGTCAGGA |
| TNF-R1 | mouse | GGGCACCTTTACGGCTTCC | TCTCCTTACAGGGGATTGTCAC |
| TGFβ1 | mouse | CTCCCGTGGCTTCTAGTGC | GCCTTAGTTTGGACAGGATCTG |
| Fibronectin | mouse | ATGTGGACCCCTCCTGATAGT | GCCCAGTGATTTCAGCAAAGG |
| Collagen | mouse | CTGTAACATGGAAACTGGGGAAA | CCATAGCTGAACTGAAAACCACC |

Statistical Analysis:

Results are presented as mean±S.E.M Data were assessed with analysis of variance (one-way ANOVA) followed by Dunnett's multiple comparisons test. Two-tailed unpaired T-test was used for comparisons between two groups. Values with statistical significance are indicated as *p<0.05, p<0.01 and *p<0.01.

Example 1. Dose Dependent Anti-Fibrotic Activity of the RUNX1 Inhibitor Ro24-7429

Bleomycin triggers a strong inflammatory response in the lung at day 7 characterized by infiltration with neutrophils and macrophages, vascular leakage, and up-regulation of cytokines, chemokines and other inflammatory mediators. By day 14, bleomycin treated mice are expected to develop significant lung fibrosis including disruption of the normal lung architecture, thickening of the alveolar septa, and excessive extracellular matrix and collagen deposition around the alveolar structures. We examined the effects of escalating doses of Ro24-7429 (17.5, 35 and 70 mg/kg per day) on bleomycin-induced lung fibrosis by H&E and Masson's trichrome staining in mice at day 14 (FIG. 1A-B, FIG. 5A-B). These doses were estimated to be equivalent to those used in the Ro24-7429 human trial, 75, 150 or 300 mg per day, respectively (28). We initiated treatment 1 week before intratracheal instillation of bleomycin because treatments for COVID-19 appear to be more effective at early stages before the disease significantly alters pulmonary function and because future clinical trials may be more feasible under a preventative therapy paradigm.

Dense areas of fibrotic foci were prominently detected two-weeks after bleomycin instillation using Masson's trichrome staining and confirmed by transmission electron microscopy (TEM) (FIG. 1A-C). Conversely, mice treated with Ro24-7429 (70 mg/kg) displayed robust preservation of lung structures after bleomycin instillation, similar to mice instilled with intratracheal saline (FIG. 1A-B, FIGS. 5A-B). Fewer to no areas of fibrosis were observed in the Ro24-7429 treated mice as confirmed by a significant reduction in the Ashcroft fibrosis score (FIG. 1D). A dose dependent effect of the drug was observed on the lung phenotype with the lowest dose (17.5 mg/kg) showing slight effect, whereas the 35 mg/kg dose showed a moderate but variable effect on the progression of fibrosis (FIGS. 5A-B).

Example 2. RUNX1 Inhibition Curbs Expression of Fibrosis Markers in Injured Mouse Lungs We evaluated the expression of RUNX1 and known markers of fibrosis in lung tissue of mice instilled with bleomycin treated with Ro24-7429 or vehicle. As expected, western blot analysis showed that Ro24-7429 treatment reduced the expression of RUNX1 and fibronectin whereas it preserved the expression of E-Cadherin, an epithelial marker (FIG. 1E-F). Quantitative RT-PCR (qRT-PCR) analysis showed upregulation of mRNA expression for fibrosis markers including α-SMA, collagen 3A1, andfi-bronectin in lung tissue of mice instilled with bleomycin compared to tissues from the saline group (FIG. 1G). Immunofluorescence staining and qRT-PCR revealed a significant upregulation of RUNX1 upon induction of fibrosis post bleomycin instillation (FIG. 1G-H). This effect on RUNX1 upregulation observed in bleomycin-injured mice was significantly attenuated in mice treated with Ro24-7429.

Ro24-7429 treatment also blunted the upregulation of fibrosis markers triggered by bleomycin compared to vehicle treated mice (FIG. 1E-H).

The protective effects of the highest dose of Ro24-7429 (70 mg/kg) were further supported by immunostaining analysis of α-SMA, a marker of scar-forming myofibroblasts, which co-localized within dense fibrotic regions in the bleomycin instilled lungs but was localized only to vessels (staining mural cells), as expected, in the Ro24-7429-treated mice (FIG. 1H).

Example 3. Anti-Inflammatory Activity of Ro24-7429

We evaluated the potential effect of Ro24-7429 on bleomycin-induced inflammation 1 week and 2 weeks after lung injury (FIGS. 1I-J and 2). As expected, bleomycin did not trigger significant fibrosis at the 1-week time point (FIG. 2 A-G). As shown in FIGS. 1I-J and 2H-I, a large influx of neutrophils and macrophages was observed in the bleomycin injected mice. Mice treated with Ro24-7429 showed reduced infiltration of inflammatory cells, specifically neutrophils and macrophages at the 1-week and 2-week time points. These results indicated that RUNX1 inhibition robustly abrogated lung fibrosis and inflammation in a bleomycin injury model.

Example 4. RUNX1 Regulates Proliferation and TGF-β1-Induced Fibrosis in Cultured Lung Cells We conducted mechanistic studies in cell culture to examine the cellular and molecular mechanisms underlying the robust effects of RUNX1 inhibition in the protection against bleomycin-induced lung injury. We tested the effect of RUNX1 inhibition on the proliferation of a human alveolar basal epithelial cell line (A549), primary human-derived pulmonary alveolar epithelial cells (HPAEpi), and in human-derived primary culture lung fibroblasts (HLF). For specific analyses we used escalating doses of Ro24-7429 (50-200 μM), Ro5-3335 (150 μM), pirfenidone (500 μg/ml) and nintedanib (5 μM), the latter two are currently approved drugs for IPF.

Ro24-7429 strongly inhibited the proliferation of A549 and HLF cells in a dose-dependent manner, as measured by the CyQUANT Direct Cell Proliferation Assay (FIG. 6). Very low levels of cell death were detected by LDH analysis at concentrations with Ro24-7429 concentrations (50-200 μM) and Ro5-3335 (150μM) in both the cell types suggesting a direct effect in proliferation by RUNX1 inhibition (FIG. 6). At 48 hours, Ro24-7429 treatment significantly reduced proliferation in A549 cells by 68% at the highest concentration (200 μM), 62% percent reduction with the lowest concentration (50 μM). We observed further reduction in proliferation at 72 hours with an 82% reduction (200 μM). A similar significant effect was observed on proliferation in HLF cells. At 72 hours, Ro24-7429 at the highest concentration (200 μM) caused a 55% reduction in proliferation. Whereas a 30% reduction in proliferation was observed at the lowest concentration (50 μM). Ro5-3335 also exhibited a strong anti-proliferative effect at 48 hours (32%) and 72 hours (50%) in A549 cells. We also observed a similar robust effect of Ro5-3335 in HLF cells resulting in a 40% reduction in proliferation at 72 hours. The effect of Ro24-7429 on proliferation was robust and of similar magnitude compared to that of nintedanib and pirfenidone. However, pirfenidone (500μ α-SMA g/ml) caused significant cell death (8%) at 48 hours, which increases to 11% at 72 hours in A549 cells (FIG. 6B).

We evaluated the effect of RUNX1 inhibition on the expression of fibrosis markers induced by TGF-β1, a critical mediator of PF (30), in A549 cells at 24, 48 and 72 hours. We found that TGF-β1 exposure strongly induced the expression of α-SMA and N-Cadherin in A549 cells using qRT-PCR (FIG. 3A) and Western blot analyses (FIG. 3B-C) at all three time points post exposure. RUNX1 expression was also strongly induced by TGF-β1 exposure at 24, 48 and 72 hours (FIG. 3A-C). We found that RUNX1 inhibition with Ro24-7429 (150 μM and 200 μM) administered 24 hours prior to TGF-β1 exposure effectively prevented TGF-β1-induced N-Cadherin upregulation in A549 cells and HPAEpi using Western blot analysis (FIG. 3D-G). We concluded that modulation of TGF-β1-mediated effects on lung fibrosis in lung epithelial cells is a potential mechanism explaining the robust impact of RUNX1 inhibition on the outcomes of bleomycin-induced lung injury.

Example 5. TNF-α Significantly Increased RUNX1 Expression in Primary Lung Endothelial Cells Pro-inflammatory mediators, such as TNF-α are increased in the inflammatory phase of tissue injury leading to fibrosis (31). This cytokine has been found to be highly elevated in patients infected with SARS-CoV-2 (24). We assessed the effect of TNF-α stimulation (5 ng/ml) on RUNX1 expression in human microvascular endothelial cells from lung (HMEC-Ls) primary cultures by immunofluorescence, qRT-PCR and Western blot. TNF-α stimulation alone increased RUNX1 staining compared to controls, whereas RUNX1 staining did not change upon exposure to TGF-β1 (FIG. 3H). A time course experiment demonstrated that RUNX1 mRNA increased by 2-fold at 48 and 72 hours post TNF-α stimulation (FIG. 3I). Ro24-7429 treatment (75 μM) significantly reduced TNF-α-induced upregulation of RUNX1 mRNA by 50% (FIG. 3J) at 48 hours. Similarly, treatment with another RUNX1 inhibitor, AI-14-91 (1 μM) (23) blunted TNFα-induced upregulation of RUNX1 mRNA by 50% at 48 hours (FIG. 3J). This data demonstrates an inflammatory cytokine-linked mechanism in lung endothelial cells, which potentially explains the robust impact of RUNX1 inhibition on the inflammatory phase of bleomycin-induced lung injury via regulation of vascular endothelial cell function.

Example 6. RUNX1 Expression in COVID-19 Lung Tissue and Modulation of Critical SARS-CoV-2 Uptake Proteins by RUNX1

We examined RUNX1 expression in seven postmortem lung tissue from patients deceased from COVID-19 and one control patient by immunohistochemistry. We found abnormal distribution of RUNX1 expression in a subset of SARS-CoV-2 virus infected lungs from two out of seven deceased cases, localized to vessels endothelia and small capillaries. Five out of seven cases presented with fibrosis and diffuse alveolar damage. Localized RUNX1 signal was not associated with pathologic presentation, though one RUNX1 positive case presented with viral load in formalin-fixed paraffin-embedded (FFPE) lung tissue (FIG. 4A; FIGS. 8-9; Table 2). Overall, these findings highlight the possibility that RUNX1 might be a novel target to ameliorate lung pathology in severe COVID-19.

We further evaluated a potential functional link between RUNX1 function and the expression of ACE2 receptor and FURIN, a proprotein convertase, which are critical for SARS-CoV-2 virus uptake within host cells using our bleomycin-induced lung injury model and TGFβ/TNF-α-stimulated lung epithelial and vascular endothelial cells in vitro.

Immunofluorescence analysis of the 2-week time point in the bleomycin mouse model showed ACE2 expression localized to the areas with increased α-SMA staining and fibrosis. Ro24-7429 treatment markedly reduced ACE2 staining and fibrosis in the lung (FIG. 4B). Additionally, we studied the effect of RUNX1 inhibition on the expression of ACE2 expression in TGF-β1 and TNF-α stimulated HPAEpi cells. We found that TGF-β1 and TNF-α exposure triggered upregulation of ACE2 protein levels (FIG. 4C-D). RUNX1 inhibition significantly reduced TGF-β1 and TNFα induced ACE2 protein levels in HPAEpi cells. FURIN protein levels were also observed to go down by 70% in the Ro24-7429 treated mice as evaluated by Western blot (FIGS. 4E-F).

We stimulated HMEC-Ls with TNF-α (5 ng/ml) to further examine the link between RUNX1 function and FURIN expression using qPCR analysis. Ro24-7429 significantly reduced FURIN mRNA expression by 70% (FIG. 4G) whereas AI-14-91 reduced mRNA expression by 50%. Because RUNX1 inhibition blunts the expression of ACE2 and FURIN in a mouse model of lung injury and in human epithelial and vascular endothelial cells in vitro this modality of treatment may have a role for the treatment of COVID-19 (FIG. 4H).

Figure 41:
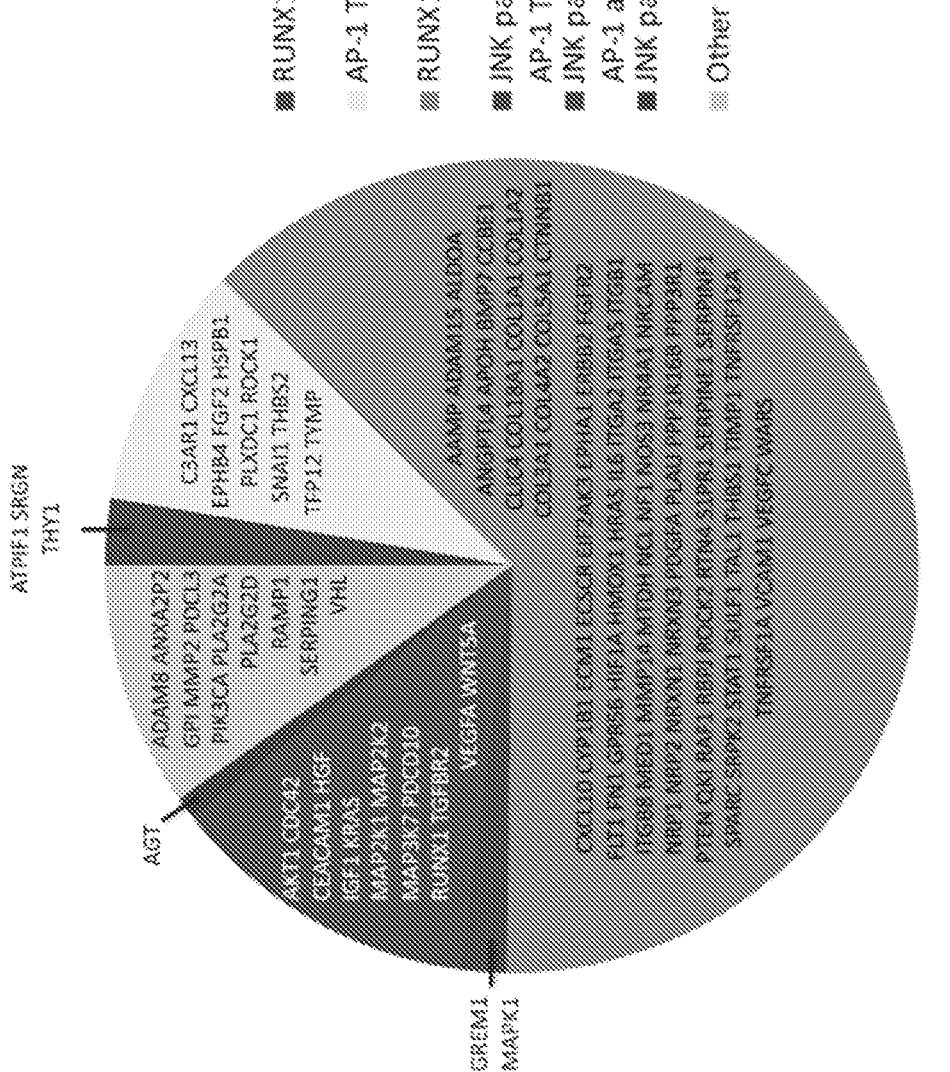

Relative changes in expression of angiogenesis-associated genes have been identified by others in the lungs of COVID-19 patients (15). Of the 113 reported genes, 100 were seen to have a relative increase in gene expression in COVID-19 patients compared to controls. We used oPOSSUM software to map RUNX1 or AP-1 (previously shown to drive RUNX1 expression in endothelial cells) transcription factor binding site (TFBS) profiles in these 113 genes (FIG. 7). Of these, 88 genes (78%) were target gene hits for RUNX1 (Z-score 15.370; Fisher score 11.682), meaning they share conserved TFBSs, and 98 genes (87%) were target gene hits for AP-1 (Z-score 14.568; Fisher score 12.297). Manual analysis of the TFBSs demonstrated an overlap of 85 genes, which contain both AP-1 and RUNX1 TFBSs, as well as 17 genes which are strongly associated with the JNK signaling pathway. Only 12 out of 113 COVID-19 genes showed no target gene hits against an AP-1 or RUNX1 JASPAR CORE profile (FIG. 41, FIG. 7). This data supports the importance of RUNX1, as well as the JNK-AP-1-RUNX1 pathway (FIG. 4F), in the regulation of angiogenesis-associated genes, which are upregulated in a severe COVID-19 disease state that ultimately leads to patient deaths in many cases.

REFERENCES AND NOTES

1. Lederer D J, Martinez F J. Idiopathic Pulmonary Fibrosis. New England Journal of Medicine. 2018; 378(19):1811-23.
2. Selman M, Pardo A. Idiopathic pulmonary fibrosis: an epithelial/fibroblastic cross-talk disorder. Respir Res. 2002; 3(1):3.
3. Lin S, Zhang R, Xu L, Ma R, Xu L, Zhu L, et al. LncRNA Hoxaas3 promotes lung fibroblast activation and fibrosis by targeting miR-450b-5p to regulate Runx1. Cell Death & Disease. 2020; 11(8):706.
4. Graney B A, Lee J S. Impact of novel antifibrotic therapy on patient outcomes in idiopathic pulmonary fibrosis: patient selection and perspectives. Patient Relat Outcome Meas. 2018; 9:321-8.

5. Maher T M. PROFILEing idiopathic pulmonary fibrosis: rethinking biomarker discovery. European Respiratory Review. 2013; 22(128):148.

6. Vancheri C, Kreuter M, Richeldi L, Ryerson C J, Valeyre D, Grutters J C, et al. Nintedanib with Add-on Pirfenidone in Idiopathic Pulmonary Fibrosis. Results of the INJOURNEY Trial. Am J Respir Crit Care Med. 2018; 197(3): 356-63.

7. Hutchinson J, Fogarty A, Hubbard R, McKeever T. Global incidence and mortality of idiopathic pulmonary fibrosis: a systematic review. European Respiratory Journal. 2015; 46(3):795.

8. Strongman H, Kausar I, Maher™. Incidence, Prevalence, and Survival of Patients with Idiopathic Pulmonary Fibrosis in the UK. Adv Ther. 2018; 35(5):724-36.

9. Ojo A S, Balogun S A, Williams O T, Ojo O S. Pulmonary Fibrosis in COVID-19 Survivors: Predictive Factors and Risk Reduction Strategies. Pulmonary Medicine. 2020; 2020:6175964.

10. George P M, Wells A U, Jenkins R G. Pulmonary fibrosis and COVID-19: the potential role for antifibrotic therapy. The Lancet Respiratory Medicine. 2020; 8(8):807-15.

11. Eapen M S, Lu W, Gaikwad A V, Bhattarai P, Chia C, Hardikar A, et al. Endothelial to mesenchymal transition: a precursor to post-COVID-19 interstitial pulmonary fibrosis and vascular obliteration? European Respiratory Journal. 2020; 56(4):2003167.

12. Huertas A, Montani D, Savale L, Pichon J, Tu L, Parent F, et al. Endothelial cell dysfunction: a major player in SARS-CoV-2 infection (COVID-19)?European Respiratory Journal. 2020; 56(1):2001634.

13. Martines R B, Ritter J M, Matkovic E, Gary J, Bollweg B C, Bullock H, et al. Pathology and Pathogenesis of SARS-CoV-2 Associated with Fatal Coronavirus Disease, United States. Emerg Infect Dis. 2020; 26(9):2005-15.

14. Schaefer I-M, Padera R F, Solomon I H, Kanjilal S, Hammer M M, Hornick J L, et al. In situ detection of SARS-CoV-2 in lungs and airways of patients with COVID-19. Modern Pathology. 2020; 33(11):2104-14.

15. Ackermann M, Verleden S E, Kuehnel M, Haverich A, Welte T, Laenger F, et al. Pulmonary Vascular Endothelialitis, Thrombosis, and Angiogenesis in Covid-19. New England Journal of Medicine. 2020; 383(2):120-8.

16. Polak S B, Van Gool I C, Cohen D, von der Thusen J H, van Paassen J. A systematic review of pathological findings in COVID-19: a pathophysiological timeline and possible mechanisms of disease progression. Mod Pathol. 2020; 33(11):2128-38.

17. Beigel J H, Tomashek K M, Dodd L E, Mehta A K, Zingman B S, Kalil A C, et al. Remdesivir for the Treatment of Covid-19 Final Report. New England Journal of Medicine. 2020; 383(19):1813-26.

18. Dexamethasone in Hospitalized Patients with Covid-19 Preliminary Report. New England Journal of Medicine. 2020.

19. Pashaei M, Rezaei N. Immunotherapy for SARS-CoV-2: potential opportunities. Expert Opin Biol Ther. 2020; 20(10):1111-6.

20. Yzaguirre A D, de Bruijn MFTR, Speck N A. The Role of Runx1 in Embryonic Blood Cell Formation. In: Groner Y, Ito Y, Liu P, Neil J C, Speck N A, van Wijnen A, editors. RUNX Proteins in Development and Cancer. Singapore: Springer Singapore; 2017. p. 47-64.

21. Bravo J, Li Z, Speck N A, Warren A J. The leukemia-associated AML1 (Runx1)-CBFβ complex functions as a DNA-induced molecular clamp. Nature Structural Biology. 2001; 8(4):371-8.

22. Cunningham L, Finckbeiner S, Hyde R K, Southall N, Marugan J, Yedavalli V R K, et al. Identification of benzodiazepine Ro5-3335 as an inhibitor of CBF leukemia through quantitative high throughput screen against RUNX1-CBFP interaction. Proceedings of the National Academy of Sciences. 2012; 109(36):14592.

23. Illendula A, Gilmour J, Grembecka J, Tirumala V S S, Boulton A, Kuntimaddi A, et al. Small Molecule Inhibitor of CBFβ-RUNX Binding for RUNX Transcription Factor Driven Cancers. EBioMedicine. 2016; 8:117-31.

24. Whitmore H A B, Amarnani D, O'Hare M, Delgado-Tirado S, Gonzalez-Buendia L, An M, et al. TNF-α signaling regulates RUNX1 function in endothelial cells. The FASEB Journal.n/a(n/a).

25. Lam J D, Oh D J, Wong L L, Amarnani D, Park-Windhol C, Sanchez A V, et al. Identification of RUNX1 as a Mediator of Aberrant Retinal Angiogenesis. Diabetes. 2017; 66(7):1950-6.

26. Delgado-Tirado S, Amarnani D, Zhao G, Rossin E J, Eliott D, Miller J B, et al. Topical delivery of a small molecule RUNX1 transcription factor inhibitor for the treatment of proliferative vitreoretinopathy. Scientific Reports. 2020; 10(1):20554.

27. Hsu M C, Dhingra U, Earley J V, Holly M, Keith D, Nalin C M, et al. Inhibition of type 1 human immunodeficiency virus replication by a tat antagonist to which the virus remains sensitive after prolonged exposure in vitro. Proc Natl Acad Sci USA. 1993; 90(14):6395-9.

28. Haubrich R H, Flexner C, Lederman M M, Hirsch M, Pettinelli C P, Ginsberg R, et al. A randomized trial of the activity and safety of Ro 24-7429 (Tat antagonist) versus nucleoside for human immunodeficiency virus infection. The AIDS Clinical Trials Group 213 Team. J Infect Dis. 1995; 172(5):1246-52.

29. Tashiro J, Rubio G A, Limper A H, Williams K, Elliot S J, Ninou I, et al. Exploring Animal Models That Resemble Idiopathic Pulmonary Fibrosis. Frontiers in Medicine. 2017; 4(118).

30. Yue X, Shan B, Lasky J A. TGF-β: Titan of Lung Fibrogenesis. Curr Enzym Inhib. 2010; 6(2).

31. Malaviya R, Laskin J D, Laskin D L. Anti-TNFα therapy in inflammatory lung diseases. Pharmacol Ther. 2017; 180:90-8.

32. Hoyt D G, Lazo J S. Alterations in pulmonary mRNA encoding procollagens, fibronectin and transforming growth factor-beta precede bleomycin-induced pulmonary fibrosis in mice. J Pharmacol Exp Ther. 1988; 246(2):765-71.

33. Lee J, Choi J H, Joo C K. TGF-β1 regulates cell fate during epithelial-mesenchymal transition by upregulating survivin. Cell Death & Disease. 2013; 4(7):e714-e.

34. Bonniaud P, Kolb M, Galt T, Robertson J, Robbins C, Stampfli M, et al. Smad3 Null Mice Develop Airspace Enlargement and Are Resistant to TGF-β-Mediated Pulmonary Fibrosis. The Journal of Immunology. 2004; 173(3):2099.

35. Zhou T, Luo M, Cai W, Zhou S, Feng D, Xu C, et al. Runt-Related Transcription Factor 1 (RUNX1) Promotes TGF-β-Induced Renal Tubular Epithelial-to-Mesenchymal Transition (EMT) and Renal Fibrosis through the PI3K Subunit p110δ. EBioMedicine. 2018; 31:217-25.

36. Kim W, Barron D A, San Martin R, Chan K S, Tran L L, Yang F, et al. RUNX1 is essential for mesenchymal stem cell proliferation and myofibroblast differentiation. Proc Natl Acad Sci USA. 2014; 111(46):16389-94.

37. Xie T, Wang Y, Deng N, Huang G, Taghavifar F, Geng Y, et al. Single-Cell Deconvolution of Fibroblast Heterogeneity in Mouse Pulmonary Fibrosis. Cell Rep. 2018; 22(13):3625-40.

38. Frangogiannis N G. Fibroblast-Extracellular Matrix Interactions in Tissue Fibrosis. Curr Pathobiol Rep. 2016; 4(1):11-8.

39. Sainson R C, Johnston D A, Chu H C, Holderfield M T, Nakatsu M N, Crampton S P, et al. TNF primes endothelial cells for angiogenic sprouting by inducing a tip cell phenotype. Blood. 2008; 111(10):4997-5007.

40. Frater-Schröder M, Risau W, Hallmann R, Gautschi P, Bohlen P. Tumor necrosis factor type alpha, a potent inhibitor of endothelial cell growth in vitro, is angiogenic in vivo. Proc Natl Acad Sci USA. 1987; 84(15):5277-81.

41. Malaviya R, Sunil V R, Venosa A, Verissimo V L, Cervelli J A, Vayas K N, et al. Attenuation of Nitrogen Mustard-Induced Pulmonary Injury and Fibrosis by Anti-Tumor Necrosis Factor-α Antibody. Toxicological Sciences. 2015; 148(1):71-88.

42. Mukhopadhyay S, Hoidal J R, Mukherjee T K. Role of TNFα in pulmonary pathophysiology. Respiratory Research. 2006; 7(1):125.

43. Sinha P, Ware L B. Selective tumour necrosis factor receptor-1 inhibition in acute lung injury: a new hope or a false dawn?Thorax. 2018; 73(8):699.

44. Liberati N T, Datto M B, Frederick J P, Shen X, Wong C, Rougier-Chapman E M, et al. Smads bind directly to the Jun family of AP-1 transcription factors. Proc Natl Acad Sci USA. 1999; 96(9):4844-9.

45. Yan X, Xiong X, Chen Y-G. Feedback regulation of TGF-β signaling. Acta Biochimica et Biophysica *Sinica*. 2018; 50(1):37-50.

46. Ji Z, He L, Regev A, Struhl K. Inflammatory regulatory network mediated by the joint action of NF-kB, STAT3, and AP-1 factors is involved in many human cancers. Proceedings of the National Academy of Sciences. 2019; 116(19):9453.

47. Tang X, Sun L, Jin X, Chen Y, Zhu H, Liang Y, et al. Runt-Related Transcription Factor 1 Regulates LPS-Induced Acute Lung Injury via NF-κB Signaling. Am J Respir Cell Mol Biol. 2017; 57(2):174-83.

48. Bellissimo D C, Chen C-h, Zhu Q, Bagga S, Lee C-T, He B, et al. Runx1 negatively regulates inflammatory cytokine production by neutrophils in response to Toll-like receptor signaling. Blood Advances. 2020; 4(6):1145-58.

49. Glinsky G V. Tripartite Combination of Candidate Pandemic Mitigation Agents: Vitamin D, Quercetin, and Estradiol Manifest Properties of Medicinal Agents for Targeted Mitigation of the COVID-19 Pandemic Defined by Genomics-Guided Tracing of SARS-CoV-2 Targets in Human Cells. Biomedicines. 2020; 8(5).

50. Thomas G. Furin at the cutting edge: from protein traffic to embryogenesis and disease. Nat Rev Mol Cell Biol. 2002; 3(10):753-66.

51. Dubois C M, Blanchette F, Laprise M H, Leduc R, Grondin F, Seidah N G. Evidence that furin is an authentic transforming growth factor-beta1-converting enzyme. Am J Pathol. 2001; 158(1):305-16.

52. Kremer S, Breuer R, Lossos I S, Berkman N, Christensen T G, Connor M W, et al. Effect of Immunomodulators on Bleomycin-Induced Lung Injury. Respiration. 1999; 66(5):455-62.

53. Laxer U, Lossos I S, Gillis S, Or R, Christensen T G, Goldstein R H, et al. The effect of enoxaparin on bleomycin-induced lung injury in mice. Exp Lung Res. 1999; 25(6):531-41.

54. Berkman N, Kremer S, Or R, Lossos I S, Christensen T G, Goldstein R H, et al. Human recombinant interferon-alpha2a and interferon-alphaA/D have different effects on bleomycin-induced lung injury. Respiration. 2001; 68(2): 169-77.

55. Edler C, Schröder A S, Aepfelbacher M, Fitzek A, Heinemann A, Heinrich F, et al. Dying with SARS-CoV-2 infection—an autopsy study of the first consecutive 80 cases in Hamburg, Germany. International Journal of Legal Medicine. 2020; 134(4):1275-84.

56. Bataller R, Brenner D A. Liver fibrosis. J Clin Invest. 2005 February; 115(2):209-18.

57. Martin M, Lefaix J, Delanian S. TGF-beta1 and radiation fibrosis: a master switch and a specific therapeutic target-?Int J Radiat Oncol Biol Phys. 2000 May 1; 47(2):277-90.

58. Lucas P A, Warejcka D J, Young H E, Lee B Y. Formation of abdominal adhesions is inhibited by antibodies to transforming growth factor-beta1. J Surg Res. 1996 October; 65(2):135-8.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating pulmonary fibrosis in a subject, the method comprising administering an effective amount of an inhibitor of runt-related family transcription factor 1 (RUNX1) selected from Ro24-7429 (7-chloro-N-methyl-5-(1H-pyrrol-2-yl)-3H-1,4-benzodiazepin-2-amine); Ro5-3335 (7-Chloro-1,3-dihydro-5-(1H-pyrrol-2-yl)-2H-1,4-benzodiazepin-2-one); 7-fluoro-N-methyl-5-(1H-pyrrol-2-yl)-3H-1,4-Benzodiazepin-2-amine; 7-fluoro-1,3-dihydro-5-(1H-pyrrol-2yl)-2H-1,4-benzodiazepin-2-one; NSC140873; MLS000548294; MLS001048862; or NSC156594.

2. The method of claim 1, wherein the subject has a viral, bacterial, or fungal infection, or has had a chemical lung injury.

3. A method for treating pulmonary fibrosis in a subject who has a coronavirus infection, the method comprising administering an effective amount of an inhibitor of runt-related family transcription factor 1 (RUNX1) selected from Ro24-7429 (7-chloro-N-methyl-5-(1H-pyrrol-2-yl)-3H-1,4-benzodiazepin-2-amine); Ro5-3335 (7-Chloro-1,3-dihydro-5-(1H-pyrrol-2-yl)-2H-1,4-benzodiazepin-2-one); 7-fluoro-N-methyl-5-(1H-pyrrol-2-yl)-3H-1,4-Benzodiazepin-2-amine; 7-fluoro-1,3-dihydro-5-(1H-pyrrol-2yl)-2H-1,4-benzodiazepin-2-one; NSC140873; MLS000548294; MLS001048862; or NSC156594.

4. The method of claim 3, wherein the coronavirus infection is infection with SARS or SARS-CoV-2.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: PCR Primer HPRT1 Forward

<400> SEQUENCE: 1
accctttcca aatcctcagc                                                    20

<210> SEQ ID NO 2
<211> LENGTH: 17
```

<212> TYPE: DNA
<213> ORGANISM: Artificial Sequence
<220> FEATURE:
<223> OTHER INFORMATION: PCR Primer HPRT1 Reverse

<400> SEQUENCE: 2
gttatggcga cccgcag                                              17

<210> SEQ ID NO 3
<211> LENGTH: 20
<212> TYPE: DNA
<213> ORGANISM: Artificial Sequence
<220> FEATURE:
<223> OTHER INFORMATION: PCR Primer RUNX1 Forward

<400> SEQUENCE: 3
tccacaaacc caccgcaagt                                           20

<210> SEQ ID NO 4
<211> LENGTH: 19
<212> TYPE: DNA
<213> ORGANISM: Artificial Sequence
<220> FEATURE:
<223> OTHER INFORMATION: PCR Primer RUNX1 Reverse

<400> SEQUENCE: 4
cgctcggaaa aggacaagc                                            19

<210> SEQ ID NO 5
<211> LENGTH: 22
<212> TYPE: DNA
<213> ORGANISM: Artificial Sequence
<220> FEATURE:
<223> OTHER INFORMATION: PCR Primer FURIN Forward

<400> SEQUENCE: 5
tcggggacta ttaccacttc tg                                        22

<210> SEQ ID NO 6
<211> LENGTH: 20
<212> TYPE: DNA
<213> ORGANISM: Artificial Sequence
<220> FEATURE:
<223> OTHER INFORMATION: PCR Primer FURIN Reverse

<400> SEQUENCE: 6
ccagccactg tacttgaggc                                           20

<210> SEQ ID NO 7
<211> LENGTH: 21
<212> TYPE: DNA
<213> ORGANISM: Artificial Sequence
<220> FEATURE:
<223> OTHER INFORMATION: PCR Primer ACE2 Forward

<400> SEQUENCE: 7
acagtccaca cttgcccaaa t                                         21

<210> SEQ ID NO 8
<211> LENGTH: 21
<212> TYPE: DNA
<213> ORGANISM: Artificial Sequence
<220> FEATURE:
<223> OTHER INFORMATION: PCR Primer ACE2 Reverse

<400> SEQUENCE: 8

-continued

```
tgagagcact gaagacccat t                                              21

<210> SEQ ID NO 9
<211> LENGTH: 21
<212> TYPE: DNA
<213> ORGANISM: Artificial Sequence
<220> FEATURE:
<223> OTHER INFORMATION: PCR Primer HPRT1 Forward

<400> SEQUENCE: 9
tcagtcaacg ggggacataa a                                              21

<210> SEQ ID NO 10
<211> LENGTH: 21
<212> TYPE: DNA
<213> ORGANISM: Artificial Sequence
<220> FEATURE:
<223> OTHER INFORMATION: PCR Primer HPRT1 Reverse

<400> SEQUENCE: 10
ggggctgtac tgcttaacca g                                              21

<210> SEQ ID NO 11
<211> LENGTH: 21
<212> TYPE: DNA
<213> ORGANISM: Artificial Sequence
<220> FEATURE:
<223> OTHER INFORMATION: PCR Primer RUNX1 Forward

<400> SEQUENCE: 11
tggtggaggt actagctgac c                                              21

<210> SEQ ID NO 12
<211> LENGTH: 23
<212> TYPE: DNA
<213> ORGANISM: Artificial Sequence
<220> FEATURE:
<223> OTHER INFORMATION: PCR Primer RUNX1 Reverse

<400> SEQUENCE: 12
cgagtagttt tcatcgttgc ctg                                            23

<210> SEQ ID NO 13
<211> LENGTH: 20
<212> TYPE: DNA
<213> ORGANISM: Artificial Sequence
<220> FEATURE:
<223> OTHER INFORMATION: PCR Primer FURIN Forward

<400> SEQUENCE: 13
agggacgtgt atcaggagcc                                                20

<210> SEQ ID NO 14
<211> LENGTH: 21
<212> TYPE: DNA
<213> ORGANISM: Artificial Sequence
<220> FEATURE:
<223> OTHER INFORMATION: PCR Primer FURIN Reverse

<400> SEQUENCE: 14
cctgctaggt cgggatgatt c                                              21

<210> SEQ ID NO 15
<211> LENGTH: 21
<212> TYPE: DNA
<213> ORGANISM: Artificial Sequence
```

-continued

```
<220> FEATURE:
<223> OTHER INFORMATION: PCR Primer ACE2 Forward

<400> SEQUENCE: 15
ggcgacaagc acagactaca a                                              21

<210> SEQ ID NO 16
<211> LENGTH: 21
<212> TYPE: DNA
<213> ORGANISM: Artificial Sequence
<220> FEATURE:
<223> OTHER INFORMATION: PCR Primer ACE2 Reverse

<400> SEQUENCE: 16
gccatctcgt ttttcaggac c                                              21

<210> SEQ ID NO 17
<211> LENGTH: 21
<212> TYPE: DNA
<213> ORGANISM: Artificial Sequence
<220> FEATURE:
<223> OTHER INFORMATION: PCR Primer alpha-SMA Forward

<400> SEQUENCE: 17
gtcccagaca tcagggagta a                                              21

<210> SEQ ID NO 18
<211> LENGTH: 21
<212> TYPE: DNA
<213> ORGANISM: Artificial Sequence
<220> FEATURE:
<223> OTHER INFORMATION: PCR Primer alpha-SMA Reverse

<400> SEQUENCE: 18
tcggatactt cagcgtcagg a                                              21

<210> SEQ ID NO 19
<211> LENGTH: 19
<212> TYPE: DNA
<213> ORGANISM: Artificial Sequence
<220> FEATURE:
<223> OTHER INFORMATION: PCR Primer TNF-R1 Forward

<400> SEQUENCE: 19
gggcaccttt acggcttcc                                                 19

<210> SEQ ID NO 20
<211> LENGTH: 22
<212> TYPE: DNA
<213> ORGANISM: Artificial Sequence
<220> FEATURE:
<223> OTHER INFORMATION: PCR Primer TNF-R1 Reverse

<400> SEQUENCE: 20
tctccttaca ggggattgtc ac                                             22

<210> SEQ ID NO 21
<211> LENGTH: 19
<212> TYPE: DNA
<213> ORGANISM: Artificial Sequence
<220> FEATURE:
<223> OTHER INFORMATION: PCR Primer TGFBeta1 Forward

<400> SEQUENCE: 21
ctcccgtggc ttctagtgc                                                 19
```

-continued

```
<210> SEQ ID NO 22
<211> LENGTH: 22
<212> TYPE: DNA
<213> ORGANISM: Artificial Sequence
<220> FEATURE:
<223> OTHER INFORMATION: PCR Primer TGFBeta1

<400> SEQUENCE: 22
gccttagttt ggacaggatc tg                                            22

<210> SEQ ID NO 23
<211> LENGTH: 21
<212> TYPE: DNA
<213> ORGANISM: Artificial Sequence
<220> FEATURE:
<223> OTHER INFORMATION: PCR Primer Fibronectin Forward

<400> SEQUENCE: 23
atgtggaccc ctcctgatag t                                             21

<210> SEQ ID NO 24
<211> LENGTH: 21
<212> TYPE: DNA
<213> ORGANISM: Artificial Sequence
<220> FEATURE:
<223> OTHER INFORMATION: PCR Primer Fibronectin Reverse

<400> SEQUENCE: 24
gcccagtgat ttcagcaaag g                                             21

<210> SEQ ID NO 25
<211> LENGTH: 23
<212> TYPE: DNA
<213> ORGANISM: Artificial Sequence
<220> FEATURE:
<223> OTHER INFORMATION: PCR Primer Collagen Forward

<400> SEQUENCE: 25
ctgtaacatg gaaactgggg aaa                                           23

<210> SEQ ID NO 26
<211> LENGTH: 23
<212> TYPE: DNA
<213> ORGANISM: Artificial Sequence
<220> FEATURE:
<223> OTHER INFORMATION: PCR Primer Collagen Reverse

<400> SEQUENCE: 26
ccatagctga actgaaaacc acc                                           23
```